United States Patent
Bushnell et al.

[19]

[11] Patent Number: 6,110,423
[45] Date of Patent: Aug. 29, 2000

[54] HIGH-STRENGTH-ELECTRIC-FIELD PUMPABLE-FOOD-PRODUCT TREATMENT IN A SERIAL-ELECTRODE TREATMENT CELL

[75] Inventors: Andrew H. Bushnell, San Diego; Joseph E. Dunn, Vista; Reginald Wayne Clark, Del Mar; Samuel W. Lloyd, La Mesa, all of Calif.

[73] Assignee: Purepulse Technologies, Inc., San Diego, Calif.

[21] Appl. No.: 09/020,266

[22] Filed: Feb. 6, 1998

[51] Int. Cl.[7] .......................................................... A61L 2/00
[52] U.S. Cl. .................................. 422/23; 99/451; 99/483; 99/DIG. 14; 210/742; 210/243; 422/22; 422/186.04
[58] Field of Search .......................... 422/22, 23, 186.04, 422/186.03; 204/252, 273, 263, 265–267; 210/748, 243; 99/451, 483, DIG. 14

[56] References Cited

U.S. PATENT DOCUMENTS

| | | |
|---|---|---|
| 918,531 | 4/1909 | Goucher . |
| 922,134 | 5/1909 | Goucher . |
| 1,479,725 | 1/1924 | Macy . |
| 1,774,610 | 9/1930 | Parsons et al. . |
| 1,900,509 | 3/1933 | Louder . |
| 2,400,951 | 5/1946 | Reid ........................................... 99/221 |
| 2,508,365 | 5/1950 | Bierwirth .................................. 219/47 |
| 2,550,584 | 4/1951 | Mittelmann ................................ 219/39 |
| 4,434,357 | 2/1984 | Simpson et al. ......................... 219/291 |
| 4,457,221 | 7/1984 | Geren ........................................ 99/451 |
| 4,695,472 | 9/1987 | Dunn et al. ............................. 426/237 |
| 4,994,160 | 2/1991 | Doevenspeck ........................... 204/165 |
| 5,048,404 | 9/1991 | Bushnell et al. .......................... 99/451 |
| 5,185,086 | 2/1993 | Kaali et al. ............................. 210/748 |
| 5,226,106 | 7/1993 | Stirling .................................... 392/314 |
| 5,326,530 | 7/1994 | Bridges ..................................... 422/22 |
| 5,583,960 | 12/1996 | Reznik ..................................... 392/321 |
| 5,690,978 | 11/1997 | Yin et al. ................................ 426/237 |

FOREIGN PATENT DOCUMENTS 1946267 3/1971 Germany .

*Primary Examiner*—Krisanne Thornton
*Attorney, Agent, or Firm*—Fitch, Even, Tabin & Flannery

[57] ABSTRACT

A system for deactivating organisms in a food product employs a first electrode; an insulator section coupled to the first electrode, wherein the insulator section includes an insulator pinch, an opening, and a transition region interposed therein between, and wherein the opening has a larger cross-sectional area than the insulator pinch, the insulator section including a cavity, passing through the insulator pinch, the transition region, and the opening, wherein the food product is contained during deactivating of organisms; and a second electrode coupled to the insulator section, wherein the first electrode is positioned on a first side of the insulator pinch, and the second electrode is positioned on a second side of the insulator pinch, whereby an electric field formed between the first electrode and the second electrode, when a voltage is applied across the first electrode and the second electrode, passes through the insulator pinch.

43 Claims, 15 Drawing Sheets

HIGH-STRENGTH-ELECTRIC-FIELD PUMPABLE-FOOD-PRODUCT TREATMENT IN A SERIAL-ELECTRODE TREATMENT CELL

BACKGROUND OF THE INVENTION

The present invention relates to processing of pumpable food products, and more particularly to processing systems and methods for deactivating organisms in pumpable food products or foodstuffs, which systems and methods extend the shelf life of such food products or foodstuffs. Even more particularly, the present invention relates to deactivating organisms or pumpable food products or foodstuffs in a high strength electric field system treatment employing serial electrodes separated by an insulating section.

As used herein the phrases "deactivating organisms," "deactivate organisms," "deactivation of organisms" and similar phrases refer to the killing or sterilization of living organisms such as bacteria, viruses, fungi, protozoa, parasites and the like.

Substantial technical effort has been directed to the preservation of perishable fluid food products such as milk products, natural fruit juices, liquid egg products, and pumpable meat products, such as ground beef or turkey. Such liquid food products may normally contain a wide variety of microorganisms, and are excellent culture media for such microorganisms.

Practical preservation methods which have found significant commercial application predominantly utilize heat treatment such as pasteurization to inactivate or reduce microorganism population. For example, milk products are conventionally pasteurized at a minimum temperature of at least about 72° C. for 15 seconds (or equivalent time/temperature relationship) to destroy pathogenic bacteria and most of the nonpathogenic organisms, with degradative enzyme systems also being partially or totally inactivated. However, products processed in this manner are still generally unsterile and have limited shelf life, even at refrigeration temperature. The shelf life of liquid foodstuffs may be substantially extended by higher heat treatment processes such as "ultra high pasteurization", or "ultra high temperature" ("UHT") treatment, at a temperature of 140° C. for four seconds. These processes are used in conjunction with aseptic packaging to achieve complete destruction of all bacteria and spores within the food product, however, such heat treatment typically adversely affects the flavor of the food product, at least partially denatures its protein content or otherwise adversely affects desired properties of the fluid food product. Other approaches to liquid food preservation, which also have certain disadvantages, include the use of chemical additives or ionizing radiation.

The bactericidal effects of electric currents have also been investigated since the end of the 19th century, with various efforts having been made to utilize electrical currents for treating food products. Such efforts are described in U.S. Pat. Nos. 1,900,509, 2,428,328, 2,428,329 and 4,457,221 and German Patents 1,946,267 and 2,907,887, inter alia, all of which are incorporated herein by reference. The lethal effects of low-frequency alternating current with low electric field strength have been largely attributed to the formation of electrolytic chemical products from the application of current through direct contact electrodes, as well as ohmic heating produced by current flow through an electrically resistive medium. Unfortunately however, the electrolytic chemical products generated by low frequency, low strength electric field methods may be undesirable in fluid foodstuffs, and heating, as noted above, may also cause undesirable effects in the fluid foodstuffs.

As described in U.S. Pat. No. 3,594,115, incorporated herein by reference, lethal effects of high voltage arc discharges have also been attributed to electrohydraulic shock waves. The utilization of explosive arc discharges to produce microbiologically lethal shock waves has not found wide-spread application as it is not a very effective means for preserving edible liquid foodstuffs. In addition, such explosive arc discharges can produce undesirable chemical byproducts in the foodstuffs being treated.

More recently, the effect of strong electric fields (or very high strength electric fields) on microorganisms has been studied as a mechanism for reversibly or irreversibly increasing the permeability of the cell membrane of microorganisms and individual cells. The application of very high strength electric fields to reversibly increase the permeability of cells has been used to carry out cell fusion of living cells and to introduce normally excluded components into living cells. Very high strength electric fields in non-nutrient media can also have a direct irreversible lethal effect upon microorganisms with the rate of deactivation dependent upon the field strength above a critical field level and the duration of the applied very high strength electric field.

A pulsed field treatment apparatus, which uses very high strength electric field pulses of very short duration, to deactivate microorganisms in food products is shown in U.S. Pat. No. 5,235,905 (the '905 patent); and U.S. Pat. No. 5,048,404 (the '404 patent), issued to Bushnell et al., and U.S. Pat. No. 4,838,154 (the '154 patent); and U.S. Pat. No. 4,695,472 (the '472 patent), issued to Dunn et al., all of which are incorporated herein by reference. The prevention of electro-phoretic and electro-chemical effects in these apparatuses is described in U.S. Pat. Nos. 5,393,541 and 5,447,733, issued to Bushnell, et al. (the '541 patent and the '733 patent), both of which are incorporated herein by reference. Generally, in accordance with the these patents, methods and apparatuses are provided for preserving fluid foodstuffs (or pumpable foodstuffs), which are normally excellent bacteriological growth media. Such preservation is achieved by applying very high strength electric field pulses (of at least 5000 v/cm) of very short duration (of no more than about 100 microseconds) through all of the pumpable foodstuff.

By "pumpable," "liquid," or "fluid" "food product" or "foodstuff" is meant an edible, food product having a viscosity or extrusion capacity such that the food product may be forced to flow through a treatment zone, e.g., less than about 1000 poise. The products include extrudable products, such as doughs or meat emulsions such as hamburger; fluid products such as beverages, gravies, sauces, soups, and fluid dairy products such as milk; food-particulate containing food slurries such as stews; food-particulate containing soups, and cooked or uncooked vegetable or grain slurries; and gelatinous foods such as eggs and gelatins.

By "bacteriological growth medium" is meant that upon storage at a temperature in the range of 0° C. to about 30° C., the fluid foodstuff, with its indigenous microbiological population or when seeded with test organisms, will demonstrate an increase in biological content or activity as a function of time as detectable by direct microscopic counts, colony forming units on appropriate secondary media, metabolic end product analyses, biological dry or wet weight or other qualitative or quantitative analytical methodology for monitoring increase in biological activity or content. For example, under such conditions the microbiological population of a pumpable foodstuff which is a bacteriological growth medium may at least double over a time period of two days.

The compositions of typical fluid food products which are biological growth media, derived from "Nutritive Value of American Foods in Common Units", Agriculture Handbook No. 456 of the U.S. Department of Agriculture (1975), are as follows:

| FLUID FOODSTUFFS | | | | | | |
|---|---|---|---|---|---|---|
| Fluid Food Product | Water Wt % | Protein Wt % | Fat Wt % | Carbohydrate Wt % | Na Wt % | K Wt % |
| Whole Milk (3.5% fat) | 87.4 | 3.48 | 3.48 | 4.91 | .05 | .144 |
| Yogurt** | 89.0 | 3.40 | 1.68 | 5.22 | .050 | .142 |
| Raw Orange Juice | 88.3 | .685 | .20 | 10.0 | .0008 | .2 |
| Grape Juice | 82.9 | .001 | tr. | .166 | .0019 | .115 |
| Raw Lemon Juice | 91.0 | .41 | .20 | 8.0 | .0008 | .14 |
| Raw Grape-Fruit Juice | 90.0 | .48 | .08 | 9.18 | .0008 | .16 |
| Apple Juice | 87.8 | .08 | tr. | 11.9 | .0008 | .10 |
| Raw Whole Eggs | 73.7 | 12.88 | 11.50 | .90 | .12 | .13 |
| Fresh Egg Whites | 87.6 | 10.88 | .02 | .79 | .15 | .14 |
| Split Pea Soup* | 70.7 | 6.99 | 2.60 | 16.99 | .77 | .22 |
| Tomato Soup* | 81.0 | 1.60 | 2.10 | 12.69 | .79 | .187 |
| Tomato Catsup | 68.6 | 2.0 | .588 | 25.4 | 1.04 | .362 |
| Vegetable beef soup | 91.9 | 2.08 | .898 | 3.9 | .427 | .066 |

*condensed - commercial
**from partially skimmed milk

Very high strength electric fields may be applied by means of treatment cells of high-field-strength design, examples of which are described in detail by Bushnell et al. and Dunn et al. Basically, the foodstuff is, in practice, electrically interposed between a first electrode, and a second electrode. The very high strength electric field is generated between the first and second electrodes such that the very high strength electric field passes through the foodstuff, subjecting any microorganisms therein to the very high strength electric field. Generally, the second electrode consists of a grounded electrode, and a relatively higher or lower voltage potential is applied to the first electrode.

In the Bushnell et al. patents and the Dunn et al. patents, the pumpable fluid foodstuff is subjected to at least one very high strength electric field and current density electrical pulse, and at least a portion of the fluid foodstuff is subjected to a plurality of very high strength electric field and current density pulses, in a high-strength electric pulse treatment zone. In one processing technique, the liquid foodstuff is introduced into a treatment zone, or cell, between two coaxial electrodes which have a parallel configuration adapted to produce a substantially uniform electric field thereinbetween without dielectric tracking or other breakdown. By "parallel" configuration it is meant that food product passes between the electrodes, such that electric flux lines are approximately normal to direction of flow. (By "serial" configuration, in contrast, it is meant that food product passes a first electrode then a second electrode, such that electric flux lines are generally parallel to the direction of flow.). Using these parallel-configured electrodes, very high strength electric field pulses are applied to the electrodes to subject the liquid foodstuff to multiple pulse treatment by the pulsed field apparatus. In order to generate the very high strength electric field pulses, the pulsed field apparatus employs, for example, a lumped transmission line circuit, a Blumlein transmission circuit and/or a capacitive discharge circuit. Alternatively, the Bushnell et al. patents describe the use of field reversal techniques in capacitive discharge systems (or pulse forming networks) to increase the effective potential across the treatment cell. For example, by applying a short electric field pulse of very high electric field strength (e.g., 20,000 volts per centimeter) across a treatment cell for a short period of time (e.g., 2 microseconds) of one polarity, followed by abrupt reversal of the applied potential within a short time period (e.g., 2 microseconds), an effective field approaching 40 kilovolts per centimeter is achieved across the cell.

If liquid foodstuff (i.e., pumpable foodstuff) is continuously introduced into the treatment zone to which very high strength electric field pulses are periodically applied, and fluid foodstuff is concomitantly withdrawn from the treatment zone, the rate of passage of the liquid foodstuff through the treatment zone can be coordinated with the pulse treatment rate so that all of the pumpable foodstuff is subjected to at least one very high strength electric field pulse within the treatment zone. The liquid foodstuff may be subjected to treatment in a sequential plurality of such treatment zones, or cells, as is described in more detail by Bushnell et al.

SUMMARY OF THE INVENTION

The present invention provides an apparatus and method for deactivating microorganisms in a food product and for preventing or reducing the fouling of a high-energy electrode in such apparatus by a fouling agent within the food product and/or preventing or reducing electrochemical effects within the food product.

In one embodiment, the present invention can be characterized as a system for deactivating organisms in a food product. The system employs a first electrode; an insulator section coupled to the first electrode, wherein the insulator section includes an insulator pinch, an opening, and a transition region interposed thereinbetween, and wherein the opening has a larger cross-sectional area than the insulator pinch, the insulator section including a cavity, passing through the insulator pinch, the transition region, and the opening, wherein the food product is contained during deactivating of organisms; and a second electrode coupled to the insulator section, wherein the first electrode is positioned on a first side of the insulator pinch, and the second electrode is positioned on a second side of the insulator pinch, whereby an electric field formed between the first electrode and the second electrode, when a voltage is applied across the first electrode and the second electrode, passes through the insulator pinch.

In a further embodiment, the present invention can be characterized as a method of deactivating microorganisms. The method involves flowing a product containing the microorganisms past a first electrode having a first cross-sectional area; flowing the product containing the microorganisms through an insulator section having a second cross-sectional area, wherein the second-cross sectional area is smaller than the first cross sectional area; flowing the product containing the microorganisms past a second electrode; and applying a high voltage electric pulse across the first electrode and the second electrode, including directing an electric field through the insulator section including increasing the electric field density over at least a portion of the insulator section; whereby at least a portion of the microorganisms are deactivated as a result of the applying of the high voltage as the product passes through the insulator section.

BRIEF DESCRIPTION OF THE DRAWINGS

The above and other aspects, features and advantages of the present invention will be more apparent from the following more particular description thereof, presented in conjunction with the following drawings wherein:

FIG. 1 is a block diagram showing a pulsed field treatment apparatus used for deactivating microorganisms in foodstuffs, and having features of the present invention including a serially-configured pair of electrodes separated by an insulator section;

FIG. 2 is a cross-sectional view of the simplest example of a treatment cell, including a serially-configured pair of cylindrical electrodes (or serial pair of electrodes) separated by an insulator section;

FIG. 3 is an equipotential plot for the cell of FIG. 2;

FIG. 4 is a graphic representation of electric field at an inner surface of the cell of FIG. 1 approximately in a modeled region (as indicated with cross-hatching in FIG. 2);

FIG. 5 is a cross-sectional view of a cell made up of a serial pair of cylindrical electrodes separated by an insulator region in which triple points on the electrodes are moved away from a treatment area in which food product flowed by angling electrodes away from the food product at their interface with the insulator section;

FIG. 6 is an equipotential plot for the cell design of FIG. 5;

FIG. 7 is a cross-sectional view of a cell made up of a series pair of cylindrical electrodes separated by an insulator section that is pinched inwardly (i.e., of smaller diameter than the electrodes);

FIG. 8 is an equipotential plot for the design of FIG. 7;

FIG. 9 is a cross-sectional view of a cell in accordance with the further embodiment of the present embodiment in which a serial pair of cylindrical electrodes enveloped by an insulator section that forms an outer cylindrical pipe having a pinched section with a smaller diameter between the electrodes than at outlying portions of the outer cylindrical pipe and in which the spaced apart serial electrodes act as flow shapers;

FIG. 10 is an equipotential plot for the design of FIG. 9;

FIG. 11 is a cross-sectional view showing a cell having a serial pair of cylindrical electrodes separated by an insulator section, wherein insulator section has a pinched section having a smaller diameter than the diameter at the electrodes and wherein an additional insulator is used in a downstream portion of the cell as a flow shaper;

FIG. 12 is an equipotential plot for the cell design of FIG. 11;

FIG. 13 is a superposition of surface electric field plots for the cell designs of FIGS. 2, 5, 7, 9, and 11 showing electric field strength at surfaces within such cells;

FIG. 14 is an electric field plot for the cell design of FIG. 2 showing electric field strength at an inner surface of the cell and along a centerline of the cell;

FIG. 15 is an energy deposition plot for the cell design of FIG. 2 showing energy deposition per pulse at an inner surface of the cell and along a centerline of the cell;

FIG. 16 shows a field plot for a scaled up (2×) version of the cell design of FIG. 2 showing electric field strength at an inner surface of the cell and along a centerline of the cell;

FIG. 17 shows an energy deposition plot for the scaled up (2×) version of the cell design of FIG. 2 showing energy deposition per pulse at an inner surface of the cell and along a centerline of the cell;

FIG. 18 shows a field plot for a variation of the cell design of FIG. 7 having an insulator length of 14.8 millimeters, an inner diameter of 9.5 millimeters at the electrodes, and an inner diameter of the insulator pinch of 5.0 millimeters, showing electric field strength at an inner surface of the cell and along a centerline of the cell;

FIG. 19 shows an energy deposition plot for the variation of FIG. 18 of the cell design of FIG. 7 showing energy deposition per pulse at an inner surface of the cell and along a centerline of the cell;

FIG. 20 is a field plot for an additional variation of the cell design of FIG. 7 having an insulator length of 14.8 millimeters, an inner diameter at the electrodes of 14.5 millimeters, and an inner diameter at the insulator pinch of 10 millimeters showing electric field strength at an inner surface of the cell and along a center line of the cell;

FIG. 21 is an energy deposition plot for the further variation of FIG. 20 of the cell design of FIG. 7 showing energy deposition per pulse at an inner surface of the cell and along a center line of the cell;

FIG. 22 is a field plot for a further variation of the cell design of FIG. 7 having an insulator length of 92.5 millimeters, an inner diameter of 10 millimeters at the electrodes, and an inner diameter at the insulator pinch of 10.0 millimeters showing electric field strength at an inner surface of the cell and along a centerline of the cell;

FIG. 23 is an energy deposition plot for the further variation of FIG. 22 of the cell design of FIG. 7 showing energy deposition per pulse at an inner surface of the cell and along a centerline of the cell;

FIG. 24 is a cross-sectional view of a cell design similar to that shown in FIG. 7 having an overall insulator length of 29.5 millimeters, an inner diameter of 22.1 millimeters at the electrodes, and an inner diameter at the pinch in the insulator of 10 millimeters with an insulator length at the pinch of 5.1 millimeters;

FIG. 25 is a cross-sectional view of a cell design similar to that shown in FIG. 7 having an overall insulator length of 40 millimeters, an inner diameter of 22.1 centimeter at the electrodes, and an inner diameter at the pinch in the insulator of 10 millimeters with an insulator length at the pinch of 5.1 millimeters;

FIG. 26 is a cross-sectional view of a cell design similar to that shown in FIG. 7 in which an overall insulator length of 11.6 millimeters is used in combination with other dimensions similar to those of the design shown in FIG. 25;

FIG. 27 is a cross-sectional view of a cell design similar to that shown in FIG. 7 in which a transition angle of the insulator from the first electrode to the pinch and from the pinch to the second electrode is decreased to about 26°, with the length of the pinch being decreased to 10.6 millimeters and with other dimensions similar to those of the design shown in FIG. 25;

FIG. 28 is a cross-sectional view of a cell design similar to that shown in FIG. 27 employing a non-uniform, i.e., asymmetrical, insulator design in which a transition angle on an upstream side of the pinch is greater than a transition angle on a downstream side of the pinch on which the pinch has a smallest diameter of 10.2 millimeters with an overall insulator length of 40 millimeters, an upstream transition region has a length of 15.1 millimeters and a downstream transition region has a length of 24.9 millimeters and in which other dimensions are similar to those of FIG. 25.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
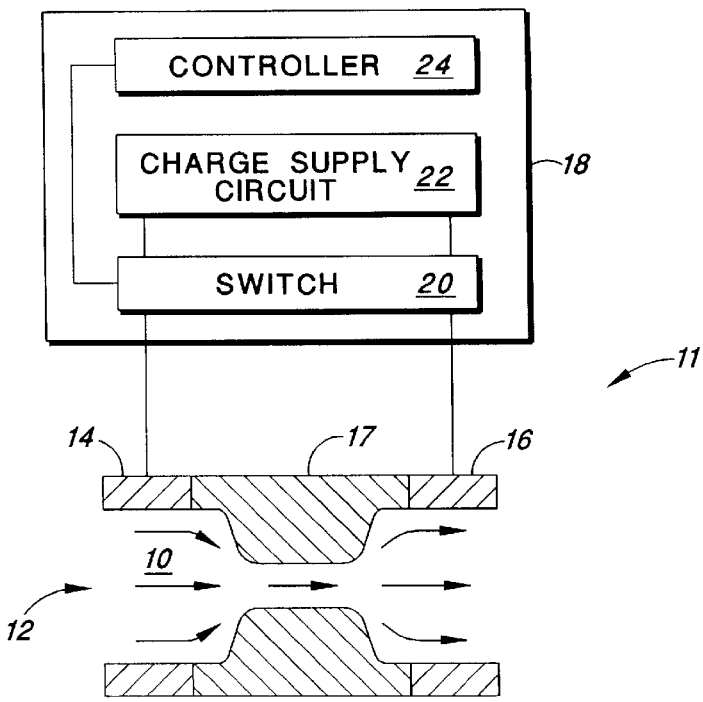

Referring first to FIG. 1, a block diagram is shown of a pulsed field treatment apparatus 11 for deactivating microorganisms in foodstuffs, food products or the like. The illustrated apparatus includes features of the present invention including a serial pair of electrodes 14, 16 separated by an insulator section 17.

A liquid foodstuff 10 or food product 10 (having a viscosity of, e.g., less than about 1000 centipoise) is circulated through a treatment zone 12 (or cell 12), as indicated in FIG. 1 by arrows, so as to interpose the foodstuff 10 or food product 10 between a first of the electrodes 14 and a second of the electrodes 16 such that electric flux lines between the electrodes 14, 16 are roughly parallel to the direction of flow of the food product. Advantageously, the first electrode 14, and the second electrode 16 have a configuration selected to produce an electric field therein-between without a high probability of dielectric tracking or other breakdown. Note that while the embodiments described herein are tailored to treatment of fluid food products, the present invention should be understood to have application to any fluid material, such as medical fluids, biological fluids, water, pharmaceuticals and other pumpable products.

The electrodes 14, 16 are separated by the insulator section 17 through which the food product 10 passes after passing through the first electrode 14 and before passing through the second electrode 16. The electrodes 14, 16 are both in the form of cylindrical pipes, such as stainless steel pipes. The insulator section may be made from plastic. The cell 12 can thus be said to comprise the electrodes 14, 16, the insulator section 17 and a circulating space within the electrodes 14, 16 and the insulator section 17 that is filled with the food product 10 as it circulates through the cell 12.

Preferably the foods product 10 has a resistivity of from about 1 to 1000 ohm-centimeters, however, the cell designs shown herein can easily be adapted for lower or higher resistivities.

Very high strength electric field pulses (having an electric field strength of at least about 5,000 volts per centimeter, and preferably at least about 10,000 volts per centimeter) are applied to the electrodes 14, 16 to subject the food product 10 to pulsed field treatment by a pulsed field treatment circuit 18.

The pulsed field treatment circuit 18 is made up of a switch 20, a charge supply circuit 22, and a controller 24. The charge supply circuit 22 supplies very high strength electric pulses to the electrodes 14, 16 selectively as determined by the switch 20. The switch 20 is controlled by a controller 24 that closes the switch 20 causing the charge supply circuit 22 to supply a very high strength electric pulse to the electrodes 14, 16. The controller 24 closes the switch 20 periodically in synchronization with a fluid flow rate of the food product 10 within the cell 12 so as to assure that all of the food product 10 is exposed to at least one very high strength electric pulse as it traverses the treatment zone within and between the electrodes (or more accurately, at least a minimum electric field strength as it traverses the treatment zone.). Pulsed field treatment circuits such as the pulsed field treatment circuit 18 are known, and suitable examples are described in the Bushnell, et al. patents and the Dunn, et al. patents previously incorporated herein by reference.

Figure 2:
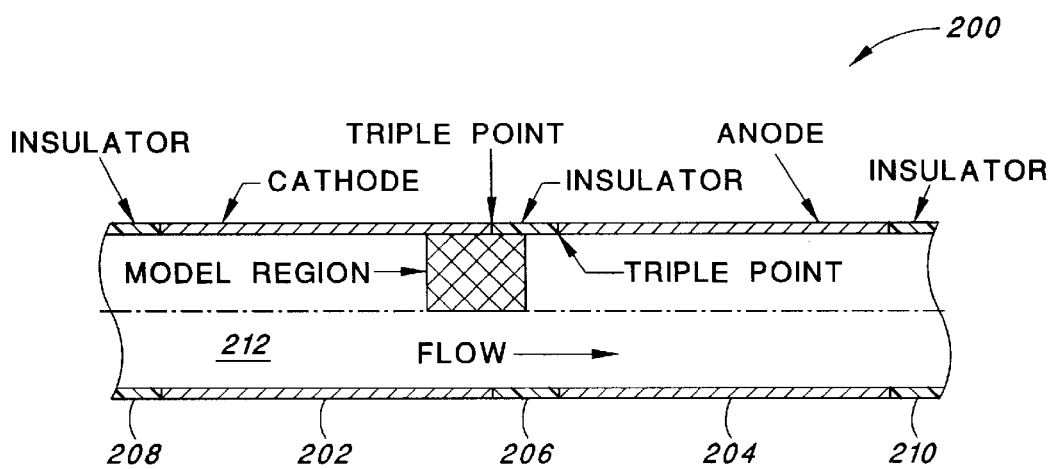

Referring next to FIG. 2, a simplest case example is shown of a cell 200 made up of a serial pair of electrodes 202, 204 separated by an insulator section 206. The cell 200 is configured as a straight cylindrical pipe having an inner diameter of 22.1 millimeters and made up of five cylindrical sections. The first of these sections is an upstream insulator section 208, the second is a first of the electrodes 202 (or a cathode 202), the third is the insulator section 206 separating the electrodes 202, 204, the fourth is a second of the electrodes 204 (or anode 204) and the fifth is a downstream insulator section 210. The electrodes 204, 206 consist of short sections of cylindrical stainless steel pipe separated by the insulator section 206 thereinbetween which is cylindrical and made from plastic. The insulator section 206 has a length of 10 millimeters.

Figure 3:
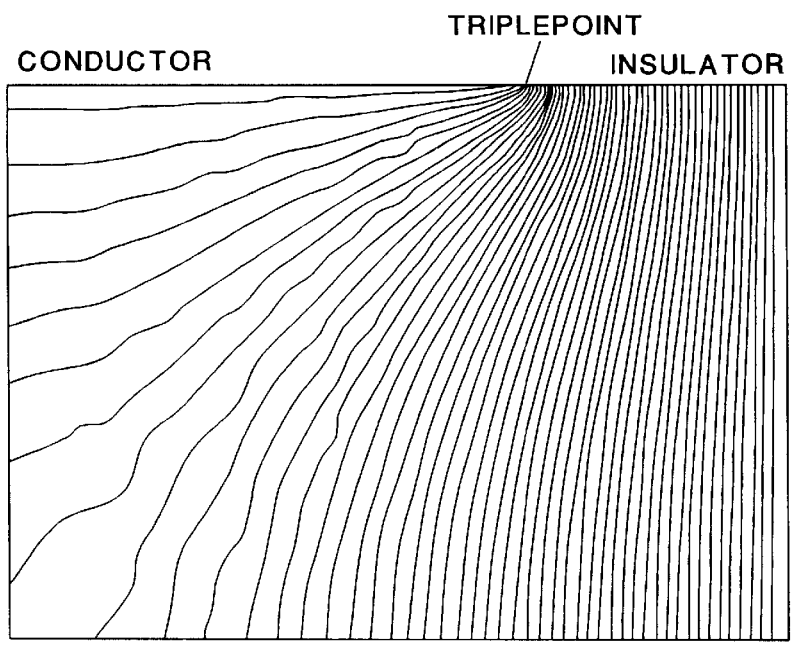
Figure 4:
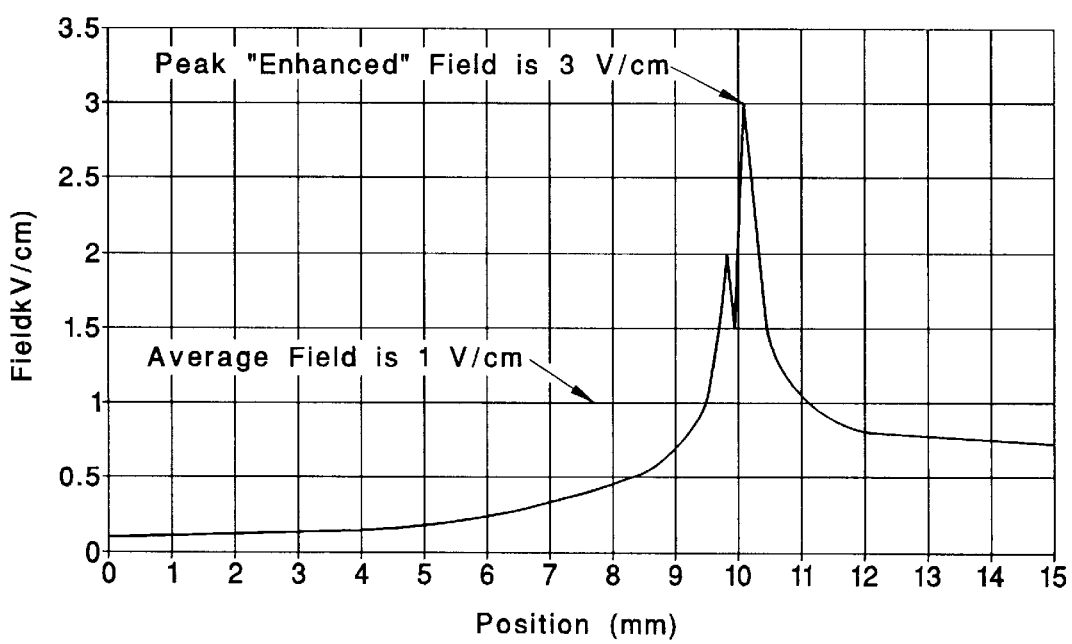

This cell's geometry, while highly desirable for cleaning and sanitizing (hermeticity), when compared to, for example, prior art coaxial cell designs, exhibits poor field distribution (see FIGS. 3 and 4). Severe enhancement of electric field at an interface between the electrodes 202, 204; the food product 212 circulating in the cylindrical pipe; and the insulator section 206 separating the electrodes 202, 204, referred to as a triple point, causes a peak electric field value of at least about three times higher than an average electric field value within the food product 212.

Problematically, these peak field values are apt to cause electrical breakdown, or arcing across the insulator and through the food product being treated. This disposition toward, i.e., probability of, arcing increases with longer electrical pulse widths and by virtue of the fact that the electric field formed between the electrodes 202, 204, when the pulsed field treatment circuit 18 is pulsed, is substantially parallel to the insulator section 206 (and food product flow) in the region of the triple point, as opposed to normal to the food product flow as with the coaxial cell designs of the prior art. Thus, while exhibiting some of the advantages of the present invention, the cell design of FIG. 2 is generally considered undesirable.

Referring next to FIG. 3, an equipotential plot is shown for the cell design of FIG. 2. The equipotential plot is taken in a modeled region designated with cross-hatching in FIG. 2. Equipotential lines in the equipotential plot show locations of points of equal electrical potential in the modeled region with each line representing 0.01 volts for 1 volt across the electrodes. Electric field lines in the modeled region are perpendicular to (normal to) the equipotential lines and electric field strength is highest where the equipotential lines are closest together. A very high relative concentration of equipotential lines present at the triple point suggests that in order to maintain an adequate minimum electric field strength (at points where electric field strength is weakest, i.e., at points where the equipotential lines are furthest apart) too high of an electric field strength would be present at the triple point. (By too high it is meant that the risk of (or probability of) dielectric tracking, arcing, or breakdown is too great for most, if not all, practical applications.) Thus, the cell design shown in FIG. 2 is considered problematic.

Referring next to FIG. 4 a plot is shown of electric field strength along an inner surface of the cell of FIG. 2 approximately in the modeled region (as indicated by cross-hatching). Electric field strength has been normalized to an average field strength of 1 V/cm. Position (in millimeters) along the surface in the modeled region is given on an abscissa (x-axis coordinate) and electric field strength (in V/cm) is given as an ordinate (y-axis coordinate). Electric field strength enhancement at the triple point is seen as a distinct peak of 3 V/cm (or three times average field strength, which is 1 V/cm).

Referring to FIGS. 5 through 30, enhancement at the triple point can be mitigated by shaping the insulators and conductors (electrodes) within the cell to alter the distribution of the electric field, i.e., to create a more uniform electric field strength distribution reducing enhancement at the triple point.

In addition, however, to analyzing electric field distribution characteristics of any cell design, in accordance with the present invention, it is also important to note that the cell design should also be analyzed for its effect on liquid food product flow patterns within the cell. Such flow analysis is important to assure that any stagnation regions present in the cell design do not result in over treatment and fouling of the liquid food product.

Each design should also be considered in view of its hygienic, i.e., cleanability, qualities.

Figure 5:
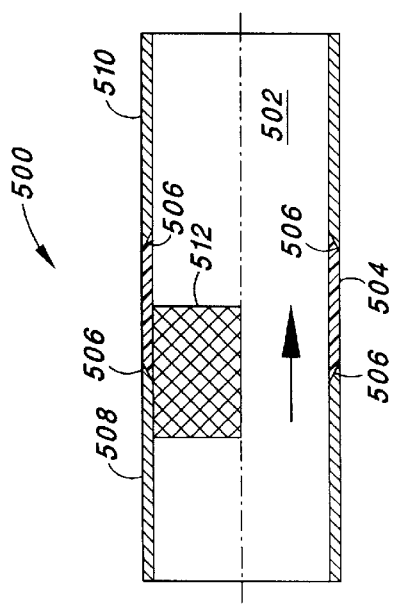

Referring specifically to FIG. 5, a cell 500 is shown in which triple points are moved away from the food product 502 and the insulator section 504 by using a frustoconical interface 506 between the electrodes 508, 510 and the insulator section 504, angling the electrodes 508, 510 away from the food product 502 at the interface 506 with the insulator section 504. Shown in FIG. 5 are the electrodes 508, 510, the insulator section 504, a modeled region 512 referenced below, the food product 502, and the frustoconical interface 506. The inner diameter at the electrodes (I.D.) is 22.1 millimeters, and the insulator length ($l_P$) is 20.6 millimeters (at the interior angling at 30° to a length of 13.3 millimeters at the exterior.)

Figure 6:
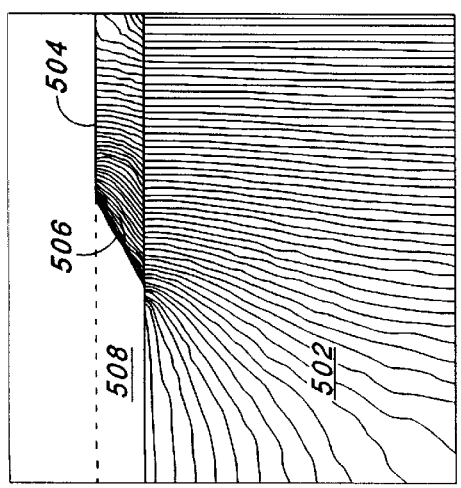

Referring to FIG. 6, an equipotential plot is shown for the design of FIG. 5. As can be seen, a very high relative electric field strength within the insulator section 504 is created relative to electric field strength within the cell, i.e., within the food product 502. When a minimum electric field strength needed to effect deactivation of microorganisms is applied throughout the cell, i.e., throughout the food product 502 in the cell, this very high relative electric field strength places a very high electromotive stress on the insulating section 504 potentially leading to failure of the insulator section 504, including potentially cracking and rupture of the cell. From a mechanical point of view, the very thin insulator section 504 thickness at the interface of the insulator section 504 with the food product and the electrodes 508, 510 could be problematic as the insulator section is prone to chipping and cracking at this interface. If the insulator section is chipped or cracked, concerns over hygienicity arise, i.e., the cell becomes difficult or impossible to clean.

Figure 7:
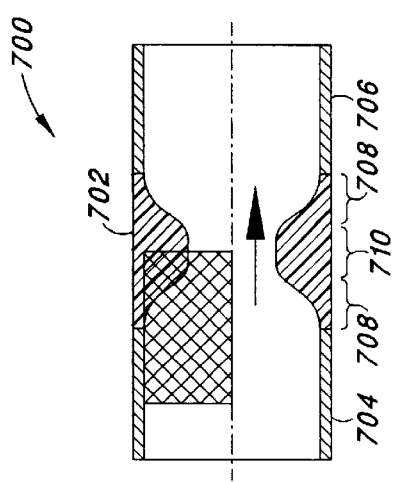

Referring next to FIG. 7, a further and generally preferred cell 700 is shown in which an insulator section 702 transitions to a smaller radius than at a first electrode 704 and then transitions back to this radius at the second electrode 706. The inner diameter at the electrodes (I.D.) is 22.1 millimeters, the insulator length ($l_i$) is 20.2 millimeters, the inner diameter at the insulator pinch (I.D.$_i$) is 11.0 millimeters, and the length of the insulator pinch ($l_p$) is 4.8 millimeters. These so-called transition sections 708 (or regions) and the corresponding region of smaller radius 710 result in concentration of current and electric field in the region of the pinch 710. The angle of the insulator section's transition relative to the electrode walls is about 45 degrees with "corners" between the transition region and the adjacent electrodes 704, 706 and insulator center section being rounded to improve fluid dynamics.

Also shown in FIG. 7, by way of example, is a flash shield 712 in the form of a disk (or more accurately, a torroid) positioned around the insulator section 702 and integral therewith. The flash shield can be formed of the same material as and be an extension of the insulator section. The flash shield may have a diameter of, for example, between 5 millimeters and 30 millimeters. The purpose of the flash shield is to inhibit tracking (arcing) between the electrodes external to the cell 700. All of the embodiments shown herein preferably include the flash shield 712 of FIG. 7, however, such is not shown, except in FIG. 7, in order to increase simplicity.

Figure 8:
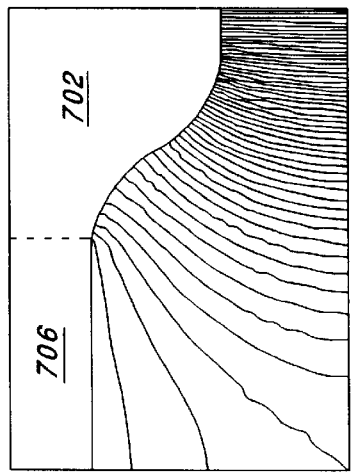

Referring to FIG. 8, an equipotential plot for the cell 700 of FIG. 7 is shown. As can be seen, the insulator section 702 does a very good job of shielding the electrodes 706, 708 from one another so that the electric field enhancement at any given point is not significant compared to the electric field strength at the center of the cell 700. This is in contrast to the cell 500 shown in FIG. 5, where significant electric field enhancement within the insulator section 504 is shown.

Figure 9:
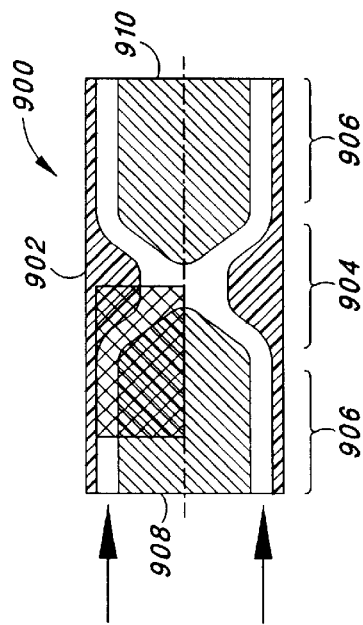

Referring next to FIG. 9, a cell 900 is shown in which an insulator section 902 makes up an entire exterior portion of the cell 900 with an insulator pinch 904 at its center having a smaller radius than a radius of the insulator at outlining areas 906. Frustoconically-tipped axial electrodes 908, 910 serve as flow shapers as well as sources of electrical potential and are generally coaxial with the insulator section 902. The inner diameter at the electrodes (I.D.) is 22.1 millimeters, the inner diameter at the pinch (I.D.$_i$) is 11.0 millimeters, an outer diameter of the electrodes (O.D.) is 17.1 millimeters, a distance between the electrodes is 6.5 millimeters, the length of the insulator pinch ($l_p$) is 6.5 millimeters.

Figure 10:
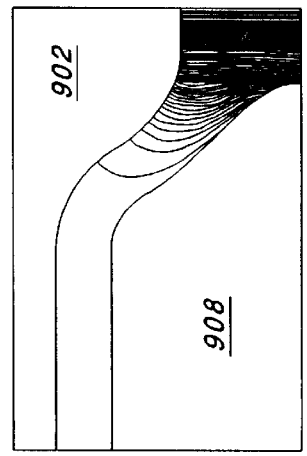

Referring to FIG. 10, an equipotential plot is shown for the design of FIG. 9. Electric field enhancement can be seen in the equipotential plot at tips of the electrodes 908, 910. These tips of the electrodes 908, 910 are also likely to be fluid stagnation points at which flow of the food product will slow or stop. As a result of these stagnation points, overtreatment of the food product and potentially fouling of the food product is likely to occur near these tips. FIG. 10 also shows that the electric field varies considerably between a surface of the insulator section 902 and a surface of the electrodes 908, 910. Thus, the embodiment of FIG. 9 is less desirable from an electric field uniformity standpoint than the embodiment of FIG. 7 although the embodiment of FIG. 9 may possess superior flow dynamics.

Figure 11:
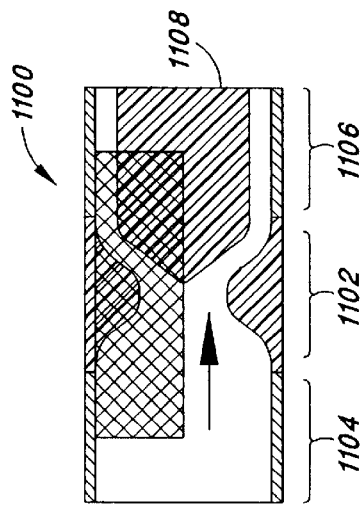

Referring to FIG. 11, a cell 1100 is shown in which an insulator pinch similar to the insulator pinch 710 of FIG. 7 is used in combination with electrodes 1104, 1106 the electrodes 704, 706 of FIG. 7, but with a frustoconically-tipped insulator 1108 serving as a flow shaper in a manner similar to that in which the second electrode 910 of FIG. 9 serves as a flow-shaper. The inner diameter at the electrodes (I.D.) is 22.1 millimeters, the length of the insulator ($l_i$) is 19.8 millimeters, the inner diameter at the pinch (I.D.$_i$) is 12.1 millimeters, an outer diameter of the frustoconically-tipped insulator is 18.1 millimeters, and a tip of the frustoconically-tipped insulator 1108 extends beyond a midpoint of the insulator pinch by 1.9 millimeters.

Figure 12:
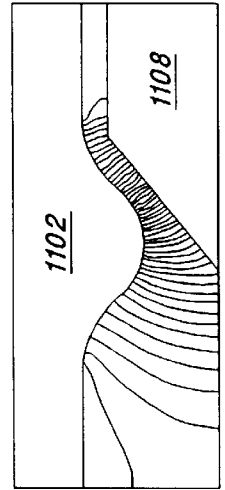

Referring to FIG. 12, an equipotential plot is shown for the cell 1100 of FIG. 11. This equipotential plot shows a fairly uniform field electric distribution in a region near the Frustoconically-tipped insulator 1108 where one would expect relatively uniform food product flow. The embodiment of FIG. 11 thus should provide a relatively uniform electric field distribution (as seen) within the cell 1100, and offer a potentially superior flow dynamic to that of the embodiment shown in FIG. 12.

Figure 13:
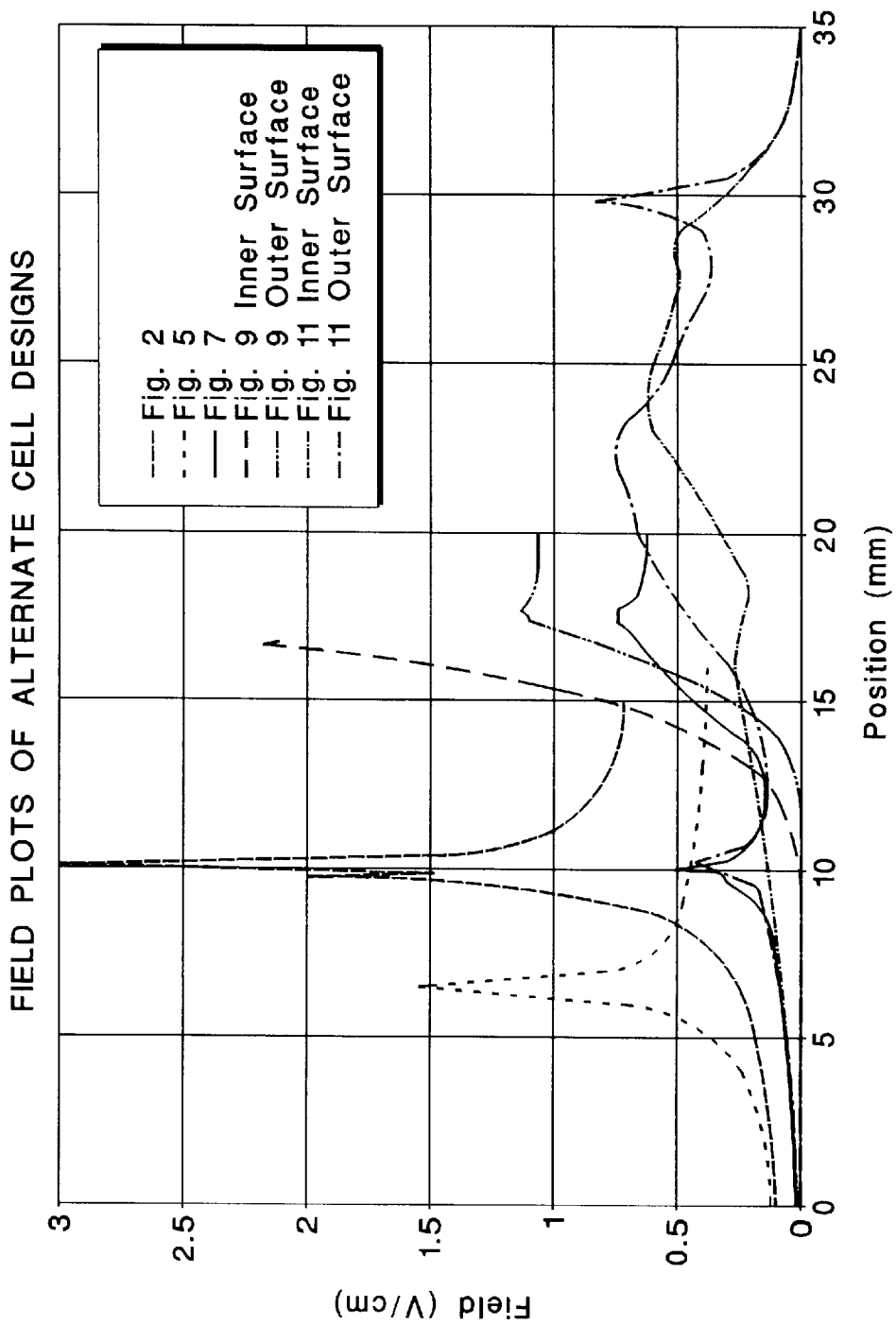

Referring next to FIG. 13, a superposition of a surface electric field plots is shown for the cells 200, 500, 700, 900, 1100 of FIGS. 2, 5, 7, 9 and 11. (Note that as represented, peak values cannot be directly compared, but must be interpreted as a function of average magnitude for each electric field plot.)

With respect to the cell 200 of FIG. 2, it can be seen on the corresponding field plot that electric field enhancement at the triple point (i.e., peak electric field strength) is very high as compared to average electric field strength for such field plot.

With respect to the cell 500 of FIG. 5, it can be seen on the corresponding field plot that field enhancement is quite high relative to average electric field strength but is improved over that shown in the field plot for the embodiment of FIG. 2.

With respect to the cell 700 of FIG. 7, it can be seen on the corresponding field plot that electric field increases near the end of the plot, which corresponds to the longitudinal center (middle) of the cell. As can be seen in the field plot for the cell of FIG. 7, the triple point is well shielded by the insulator pinch so that electric field enhancement (i.e., peak electric field strength) is not significant as compared, for example, to the peak electric field strength shown in the field plots for the cells 200, 500 having straight insulator section designs.

In the field plot corresponding to the cell 800 of FIG. 9, field levels vary considerably between an outer surface and an inner surface (i.e., the surface of the insulator and the surface of the electrodes.). Field plots showing field levels at both the surface of the insulator and at the surface of the electrodes are shown. As can be seen, significant electric field enhancement occurs at the triple points relative to average field strength.

Separate field plots corresponding to the cell 1100 of FIG. 11 show the electric field along the inner surface and the surface of such cell 100 of the Frustoconical-tipped insulator 1108 to be similar. Enhancement at the surface triple point near the first electrode 1104 is, however, observed but may be reducible with further design enhancement, such as by changing the relative positions of the Frustoconical-tipped insulator 1108, the insulator pinch 1102 and the electrodes 1104, 1106 so that the triple point is not directly opposite the corner of the Frustoconical-tipped insulator.

Figure 14:
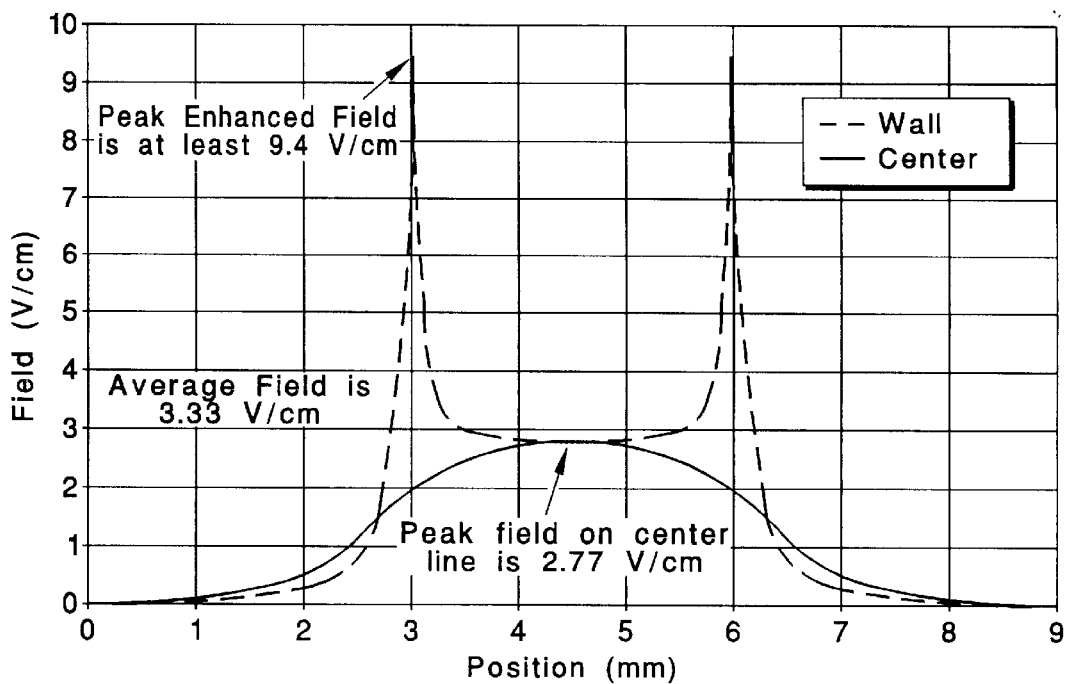

Referring next to FIG. 14, a superpositions of field plots is shown for the design similar to that of FIG. 2 having an inner diameter of 2.3 millimeters and an insulator length of 3 millimeters. The plots are shown for electric field strength at the inner surface of the cell 200 and along a centerline (or major axis) of the cell, showing very high electric field enhancement at the triple points along the inner surface of the cell 200, and showing peak fields at the longitudinal center (middle) of the cell along the centerline (or major axis) of the cell 200. The electric field along the centerline is approximately equal to the electric field at the inner surface of the cell 200 at the longitudinal center of the cell 200.

As can be seen, peak electric field is at about 9.4 volts per centimeter at the triple point, which is 3.4 times higher than the field at the centerline of the cell 200, which is about 2.77 volts per centimeter. Thus, if an electric field of, for example, 25 kilovolts per centimeter is required for effective treatment, voltage on the cell must be at least nine kilovolts to assure the minimum electric field strength 25 kilovolts per centimeter throughout the cell 200. Multiplying by the enhanced field at the triple point, it can be seen that 84.8 kilovolts per centimeter will be present at the electrode interface, i.e., at the triple points.

Figure 15:
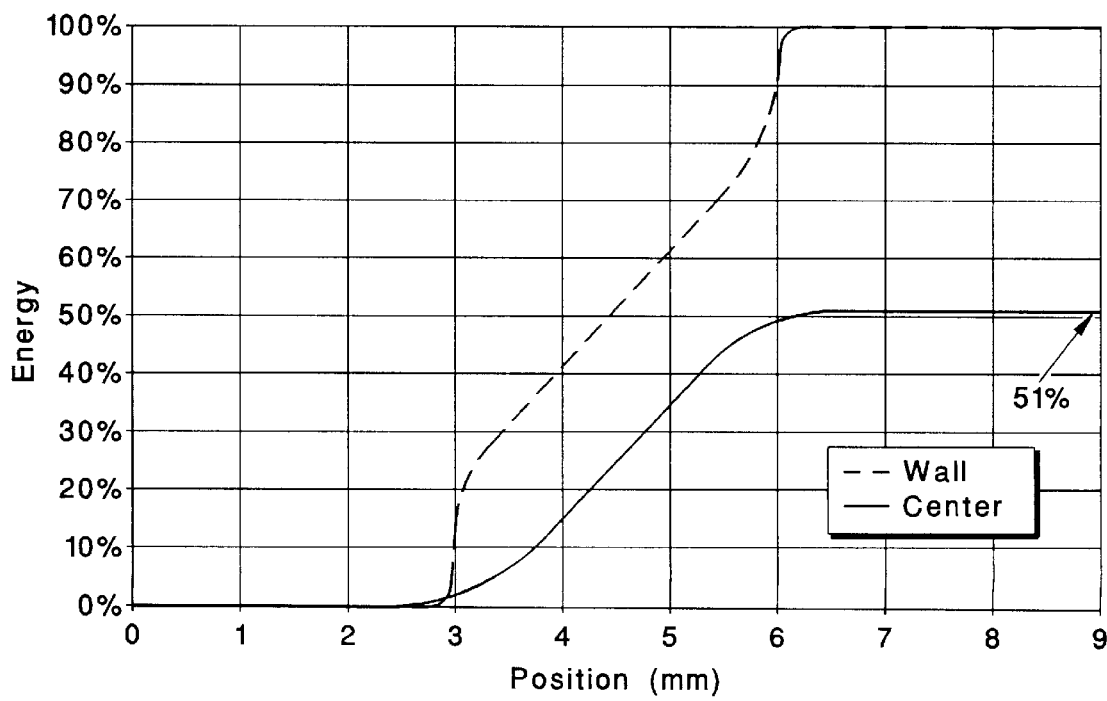

Referring next to FIG. 15, energy deposited in the food product per electrical pulse is also plotted for a cell similar to the cell 200 of FIG. 2 having the dimensions given above in reference to FIG. 14. The energy deposition plotted is at the inner surface and along the centerline. The energy deposited into the food product by a single electrical pulse is given by:

$$\text{Energy} = \frac{E^2 \cdot \tau}{\rho}$$

where E is the electrical field in kilovolts per centimeter, $\tau$ is the pulse width, and $\rho$ is the resistivity of the food product in ohm-centimeters. This calculation assumes that the food products resistivity is constant and that the flow of the food product is uniform, both of which are generally untrue, however, this calculation is still useful for best-case comparison purposes.

This calculation also assumes infinite pulse width (i.e., very closely spaced pulses), or a very high number of pulses so that a constant electric field strength is applied to the food product traversing the cell. In other words, integration for the present example (the cell similar to FIG. 2 with the dimensions given in reference to FIG. 14) is with respect to position for a food product particle traversing the cell 200 with the electric field strength shown in FIG. 14. Thus, the graph shown in FIG. 15 is relative and useful only for comparison purposes.

Note the fact that the amount of energy deposited along the centerline of the cell 200 is approximately 51% of the amount of energy deposited at the inner surface of the cell 200 when taken at the longitudinal center of the cell 200 (i.e., the energy ratio is 51%).

Figure 16:
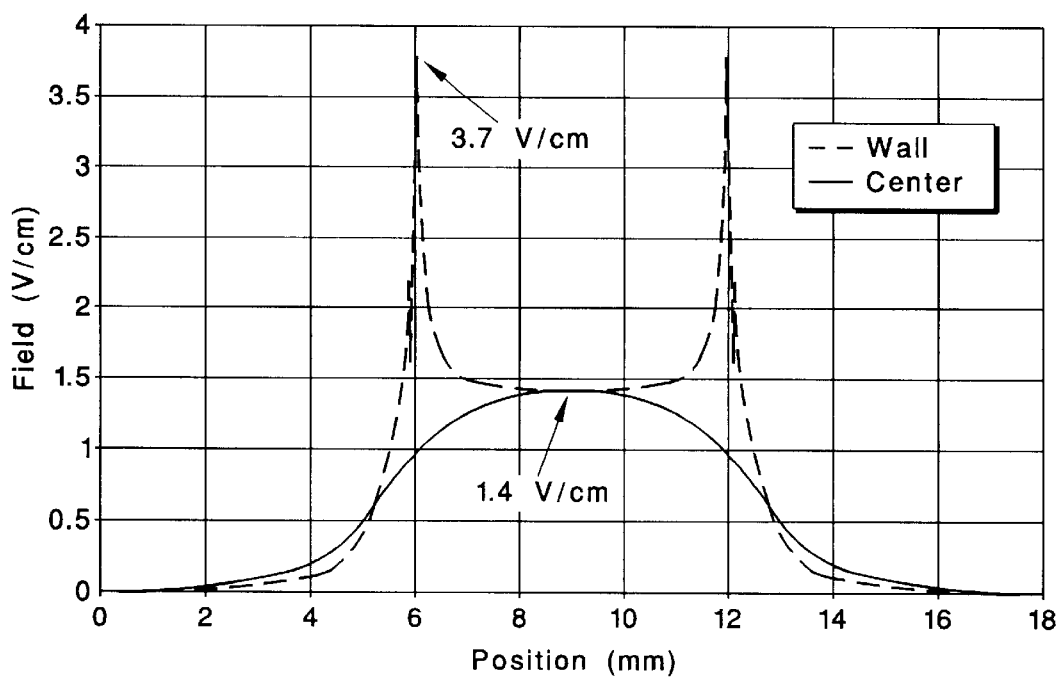
Figure 17:
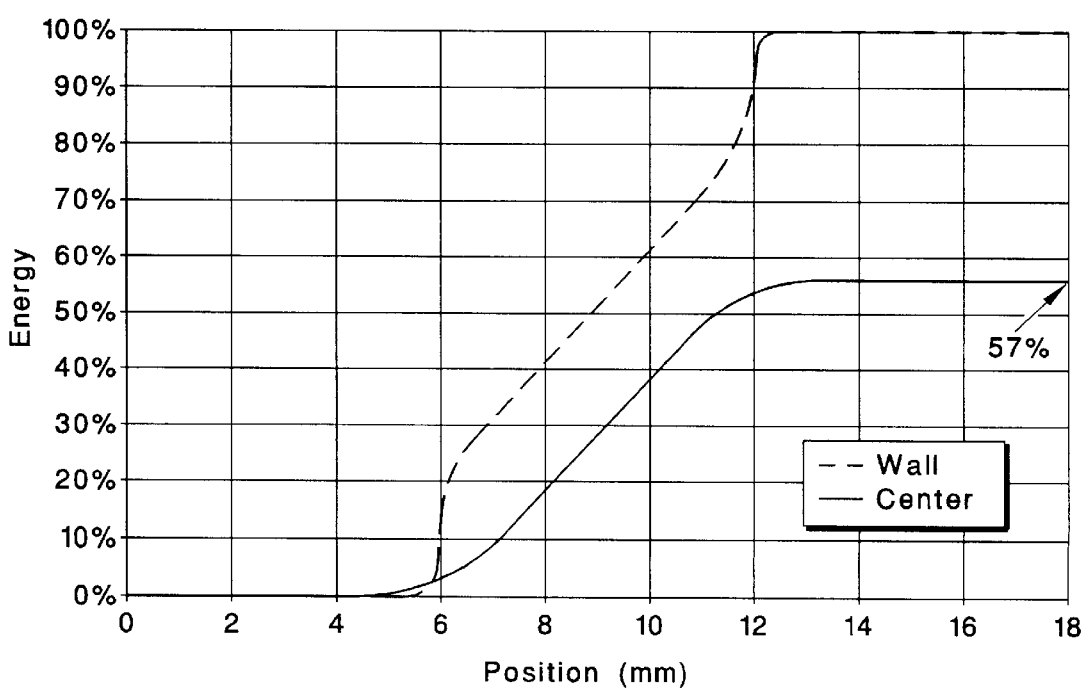

If dimensions of the cell described above in reference to FIG. 14 are scaled up by a factor of 2, such that the inner diameter (I.D.) is 4.6 millimeters and the insulator length ($l_i$) is 6 millimeters, the energy ratio goes to 57%. A field plot for a scaled up version of the cell 200 described in reference to FIG. 14 and a relative energy deposition plot for this scaled up cell are shown in FIGS. 16 and 17, respectively.

Figure 18:
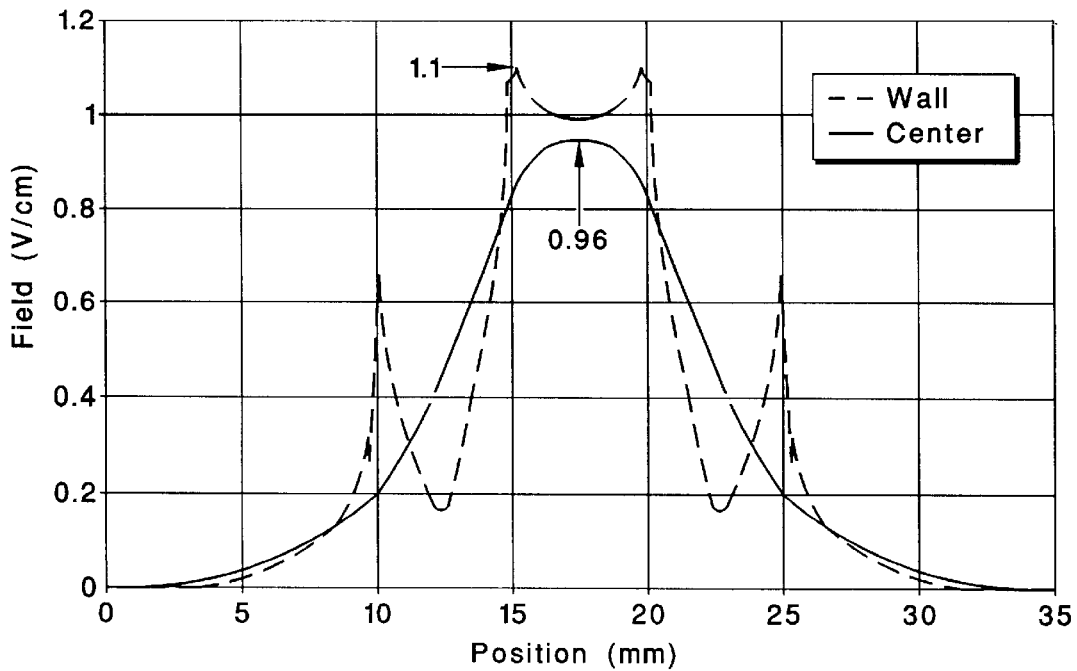

Referring to FIG. 18, a field plot is shown for a cell such as is shown in FIG. 7 having an insulator length ($l_i$) of 14.8 millimeters, an inner diameter (I.D.) at the electrodes of 9.5 millimeters and an inner diameter (I.D.$_i$) at the insulator pinch of 5 millimeters. Field strength at the wall of the cell is shown, as is field strength along the centerline of the cell.

Figure 19:
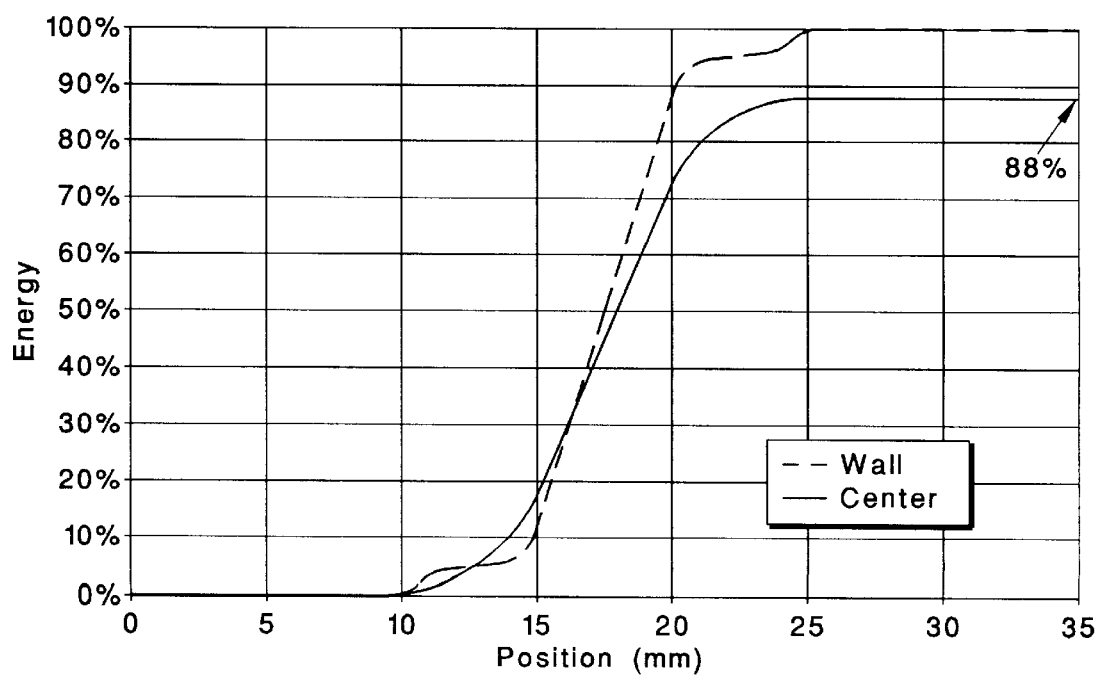

Referring next to FIG. 19, relative energy deposition is shown for a treatment cell having the dimensions specified above in reference to FIG. 18. Energy deposition at the inner surface of the cell is shown, as is energy deposition along the centerline of the cell. As can be seen, energy deposition along the centerline at the longitudinal center of the cell is about 88% of that measured at the inner surface at the longitudinal center of the cell. Thus, the energy deposition in the cell described above in reference to FIG. 18 is more uniform than for the cell of FIG. 2, either in the form shown in FIG. 2, in the form described in reference to FIG. 14 or in the scaled up variation described in connection with FIGS. 16 and 17.

Figure 20:
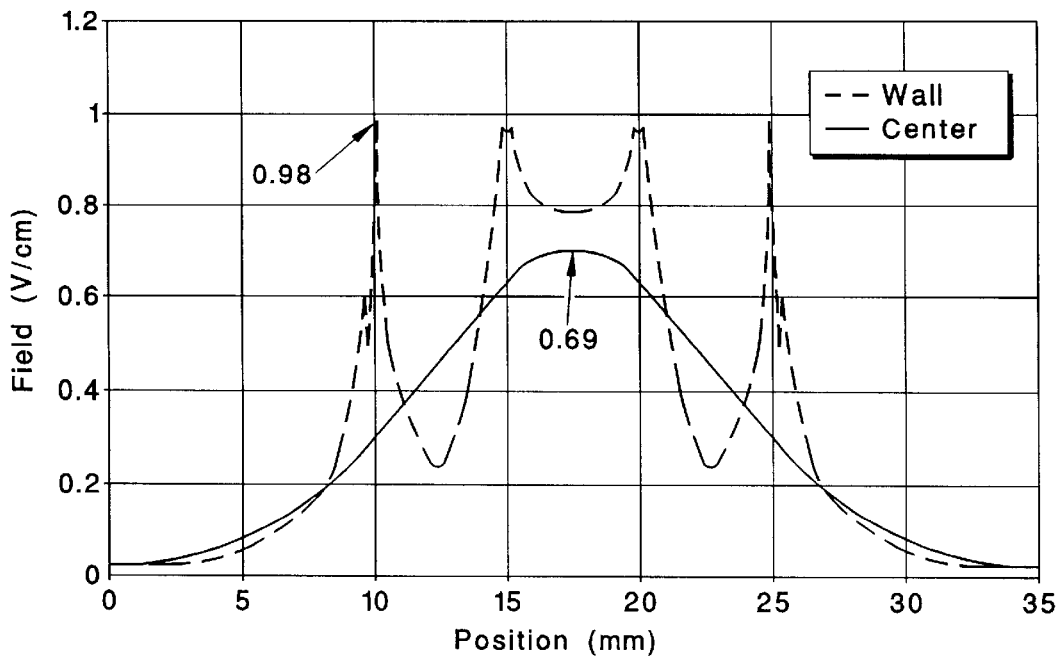

In reference to FIG. 20, field plots are shown for a cell such as shown in FIG. 7 having an insulator length ($l_i$) of 14.8 millimeters, an inner diameter (I.D.) at the electrodes of 14.5 millimeters and an inner diameter (I.D.$_i$) at the insulator pinch of 10 millimeters. Shown are field strength along the inner surface of the cell, and field strength along the centerline of the cell.

Figure 21:
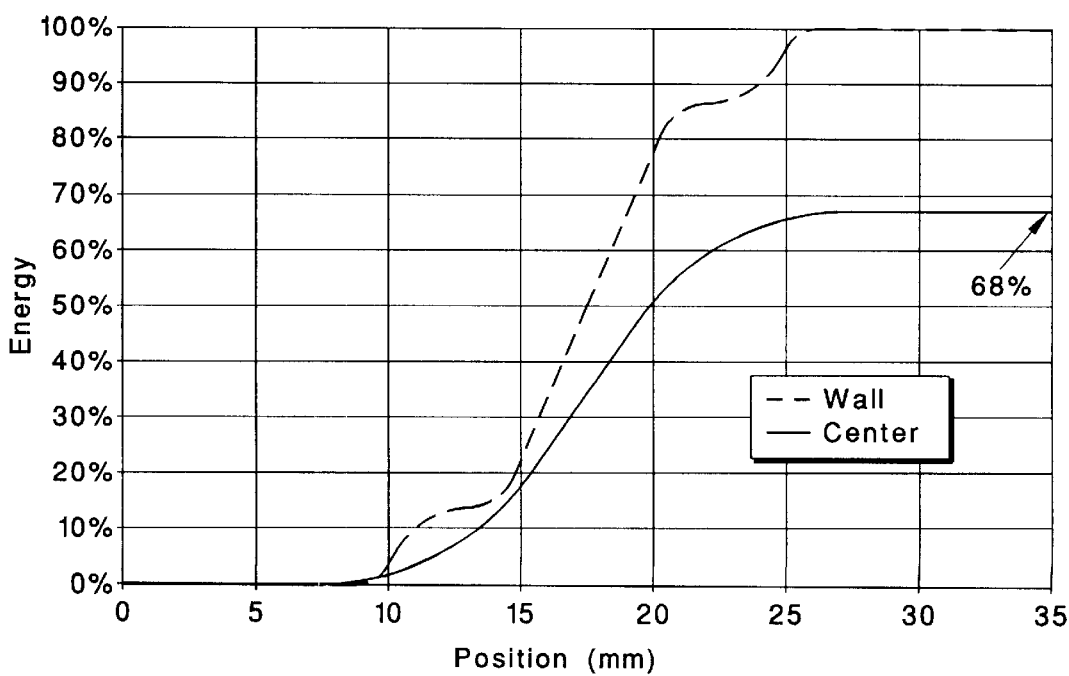

Referring next to FIG. 21, a relative energy deposition plot is shown for the cell described above in reference to FIG. 20. Shown is relative energy deposition along the inner surface of the cell, and energy deposition along a centerline of the cell. As can be seen, energy deposition along the centerline of the cell is approximately 68% of the energy deposition along the inner surface of the cell at the longitudinal center of the cell, making energy deposition in the cell having dimensions described in reference to FIG. 20 less uniform than the energy deposition in the cell having dimensions described in reference to FIG. 18.

Figure 22:
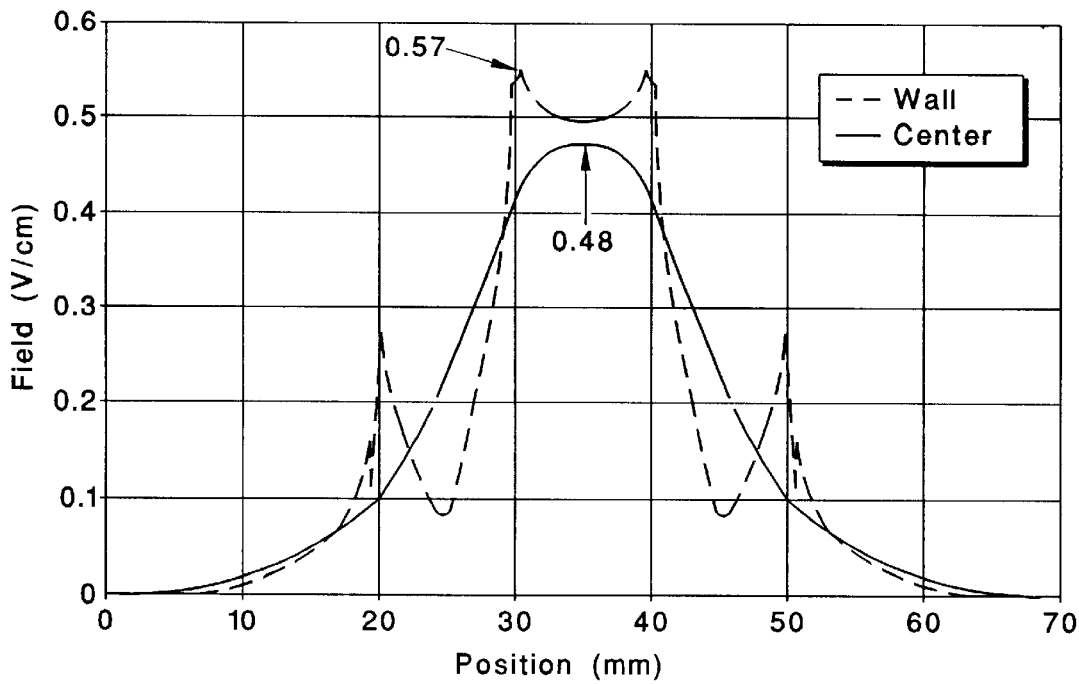

Referring next to FIG. 22, a field plot is shown for a cell such as shown in FIG. 7 having an insulator length ($l_i$) of 29.5 millimeters, an inner diameter (I.D.) at the electrodes of 19.1 millimeters and an inner diameter (I.D.$_i$) at the insulator pinch of 10 millimeters. Shown are a field plot along the inner surface of the cell, and a field plot along a centerline of the cell.

Figure 23:
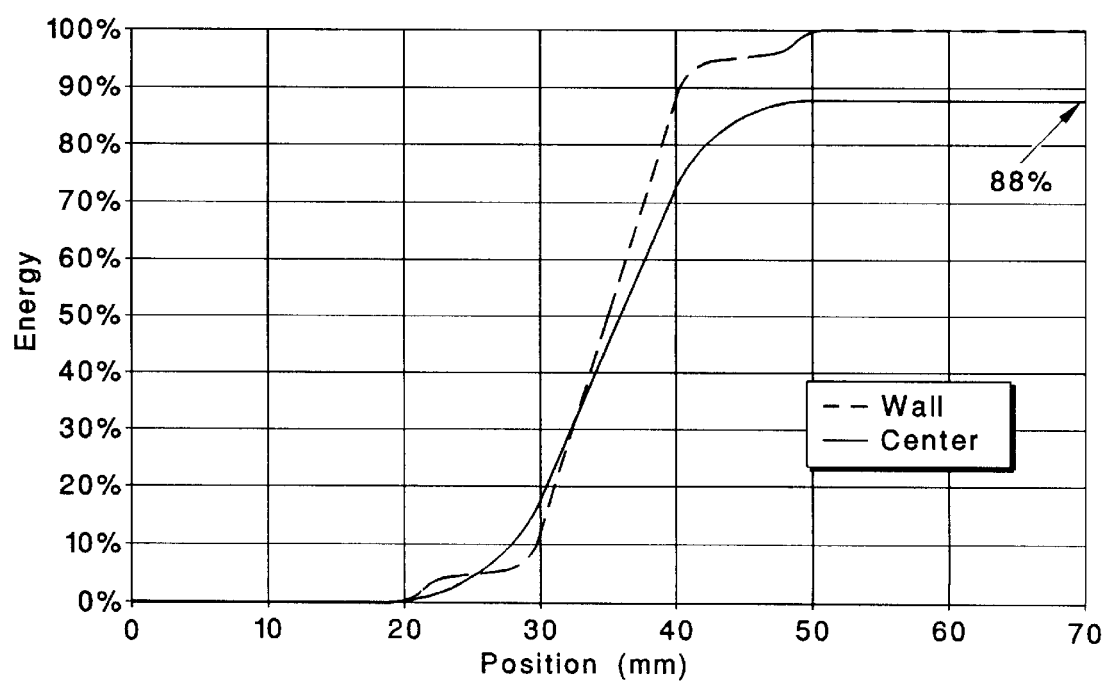

Referring next to FIG. 23, a relative energy deposition plot is shown for the cell described above with reference to FIG. 22. Shown is energy deposition along the inner surface of the cell, and energy deposition along a centerline of the cell. As can be seen, energy deposition along the centerline of the cell is about 88% of the energy deposition along the inner surface of the cell at the longitudinal center of the cell, making energy deposition in the cell having dimensions described in reference to FIG. 22 about the same in uniformity as the energy deposition in the cell having dimensions described in reference to FIG. 18.

With reference to FIGS. 18 through 23, it can thus be seen that an insulator length ($l_i$) to inner diameter at the insulator pinch (I.D.$_i$) ratio or insulator length ($l_i$) to gap (I.D.$_i$) ratio has a dramatic effect on field distribution and on energy deposition uniformity. Specifically, as the insulator length ($l_i$) to gap (I.D.$_i$) ratio decreases, the energy distribution uniformity worsens, i.e., decreases. In other words, the amount of energy deposited along the centerline at the longitudinal center of the cell becomes smaller as a percentage of the amount of energy deposited along the inner surface of the cell at the longitudinal center of the cell, as the insulator length ($l_i$) to gap (I.D.$_i$) ratio decreases.

Thus, based on the above, in an effort to achieve uniform food product treatment, the insulator length ($l_i$) to gap (I.D.$_i$) ratio should be as large as possible, i.e., the length should be as long as possible and the gap as small as possible as balanced with competing objectives, such as minimizing voltage across the cell and optimizing flow dynamics within the cell.

The minimum gap useable with a particular food product is driven by the viscosity of the food product and the amount and sizes of any solid material within the food product. The maximum length is driven by the minimum voltage needed to achieve a designed minimum electric field strength throughout the cell (or treatment zone) during each pulse.

As can further be seen in FIGS. 18 through 23, use of the insulator pinch reduces the magnitude of field enhancement at triple points and increases the magnitude of the electric field along the centerline of the cell as compared to the straight pipe design of FIG. 2. This is due to the concentration of current and electric field in the insulator pinch. This benefit of the insulator pinch, however, is potentially offset by the possible propensity for flow separation at the downstream side of the insulator pinch, which must be accounted for.

Figure 24:
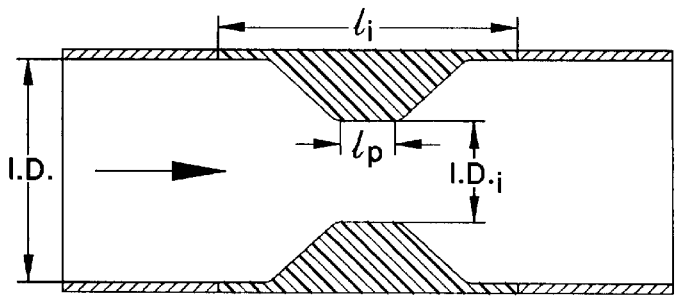

With reference to FIG. 24, a cell is shown in which an insulator length ($l_i$) of 29.5 millimeters is used with a inner diameter (I.D.$_i$) at the electrodes of 22.1 (I.D.) millimeters, an inner diameter (I.D.$_i$) at the insulator pinch of 10 millimeters and an insulator length ($l_p$) at the pinch of 5.1 millimeters. A transition angle from the first electrode to the insulator section and from the insulator section to the second electrode is between about 130° and 160°, for example, between about 135° and 145°, for example 132.8°. (Such angle is measured between an interior surface of the electrode on the frustoconical inner surface of the transition region.)

Figure 25:
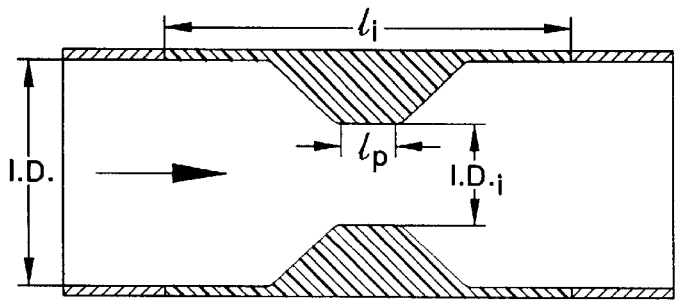

With reference to FIG. 25, a cell design is shown in which an insulator length ($l_i$) of 40 millimeters is used within an inner diameter (I.D.$_i$) at the electrodes of 22.1 millimeters an inner diameter (I.D.) at the electrodes, the 10 millimeter inner diameter (I.D.) at the insulator pinch of 10 millimeters and an insulator length ($l_p$) at the insulator pinch of 5.1 millimeters. A transition angle is similar to that described in reference to FIG. 24.

Figure 26:
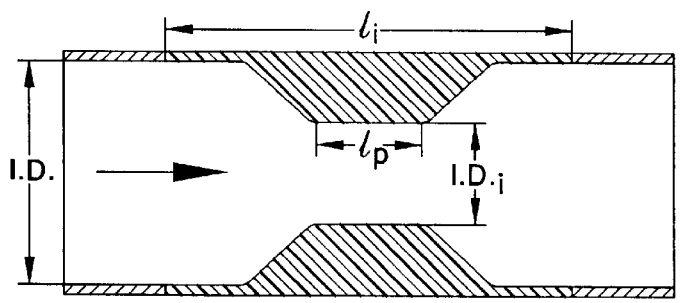

Referring next to FIG. 26, a cell is shown in which an insulator length ($l_p$) at the insulator pinch is 11.6 millimeters is used, with other dimensions of the cell shown in FIG. 25, i.e., the 22.1 millimeter inner diameter (I.D.) at the electrodes, the 40 millimeter overall insulator length ($l_i$), and the 10 millimeter inner diameter (I.D.$_i$) at the insulator pinch. A transition angle is similar to that described in reference to FIG. 24.

Figure 27:
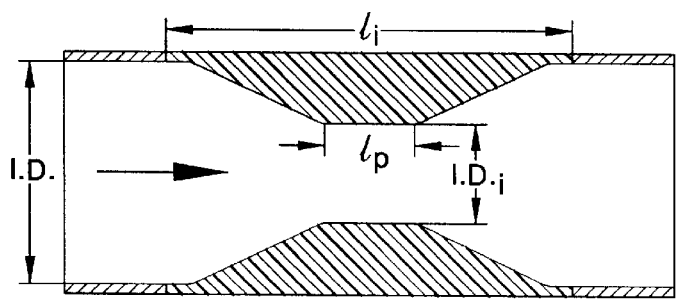

With reference to FIG. 27, the transition angle of the insulator from the first electrode to the insulator pinch and the transition angle of the insulator from the insulator pinch back to the second electrode are each decreased from between about 100° to about 175°, for example between about 135° and 145°, for example 137.8° in the cells of FIGS. 24 through 26 to between about 100° to about 175°, for example between about 145° and 155°, for example 153.7°. The insulator length ($l_p$) at the pinch is 10.6 millimeters, with other dimensions of the cell shown in FIG. 25, i.e., the 22.1 millimeter inner diameter (I.D.) at the electrodes, the 40 millimeter length ($l_i$) and the 10 millimeter inner diameter (I.D.$_i$) at the insulator pinch.

Figure 28:
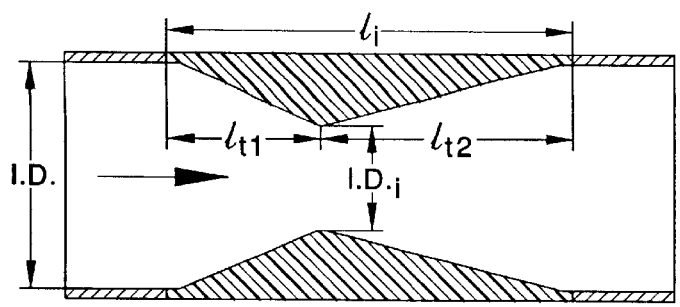

Referring next to FIG. 28, a non-uniform, i.e., asymmetrical, insulator design is shown in which a 10.2 millimeter inner diameter (I.D.) at the insulator pinch is used with a 40 millimeter insulator length ($l_i$), and a 22.1 millimeter inner diameter (I.D.) at the electrodes. Transition from the electrode inner diameter (I.D.) to the insulator pinch inner diameter (I.D.$_i$) on the upstream side occurs over a 15.1 millimeter distance ($l_{t1}$), while the transition back to the electrode inner diameter (I.D.) from the insulator pinch inner diameter (I.D.$_i$) on the downstream side of the insulator pinch occurs over a 24.9 millimeter distance ($l_{t2}$). The transition angle from the first electrode to the insulator pinch is between about 100° and 175°, for example between about 100° and 160°, for example 154°, and the transition angle from the insulator pinch to the second electrode is between about 100° and 175°, for example between about 150° and 175°, for example 166° In the example shown, the transition angle from the first electrode to the insulator pinch is about 153.7° and the transition angle from the insulator pinch to the second electrode is about 165.7°.

Figure 29:
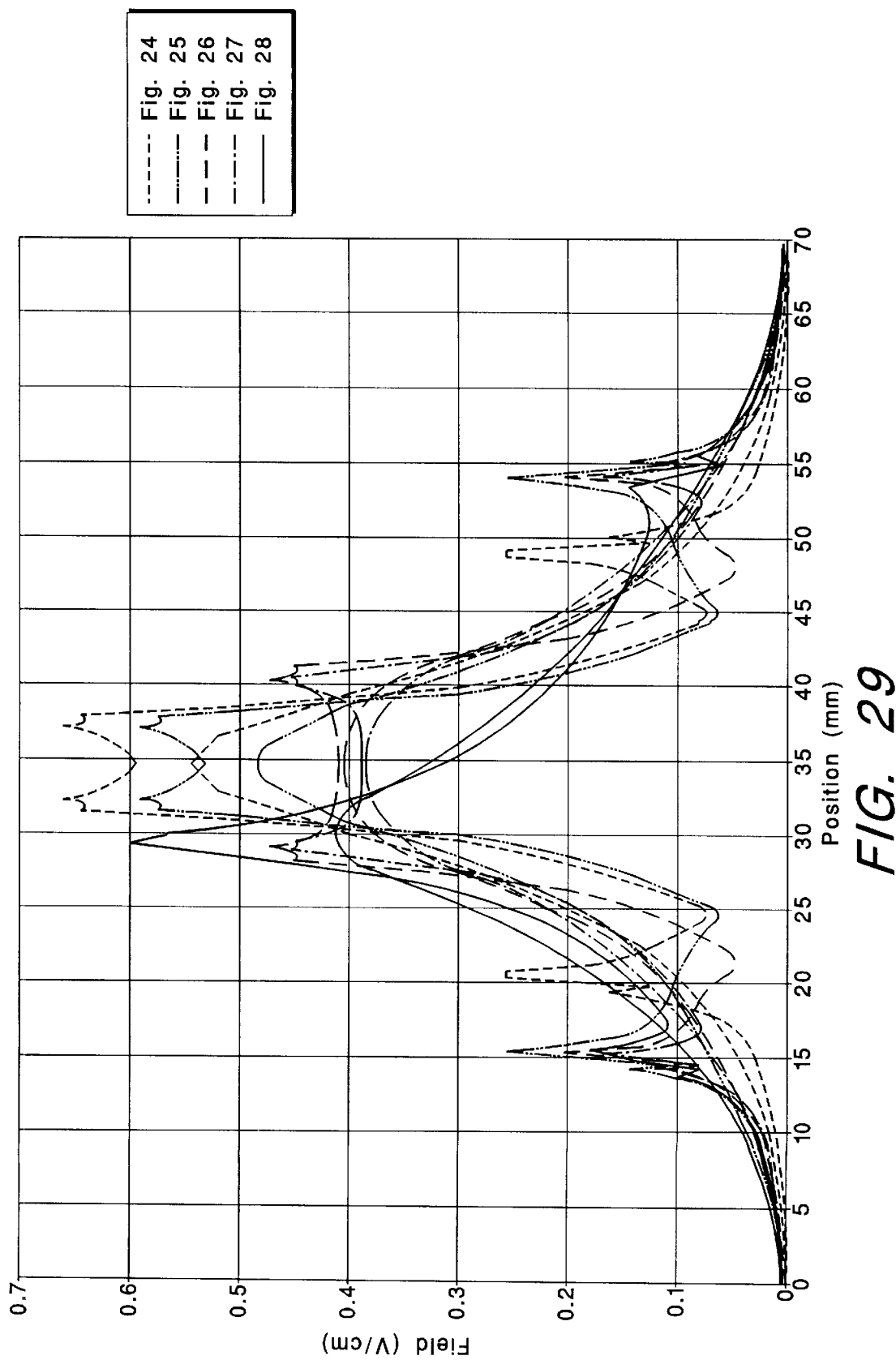
FIG. 29 is a superposition of surface electric field plots for the cell designs of FIGS. 24 through 28 showing electric field strength at inner surfaces and along centerlines of each of cell the designs of FIGS. 24 through 28.

With reference to FIG. 29 a superposition of field plots is shown comparing each of the cell design iterations illustrated in FIGS. 24 through 28. Field strength along the inner surface of such cells is shown, as is field strength along the centerline of such cells.

Each of these cells is simulated with the assumption that a maximum voltage that can be applied to the cell, i.e., across the electrodes, is 100 kilovolts and a maximum current in the switch (FIG. 1) is limited to 15 kiloamps. A minimum electric field strength to effect deactivation of microorganisms is used in determining the chamber voltage and is selected as 25 kilovolts per centimeter and thus serves as a minimum electric field strength that must be present throughout the treatment region, i.e., insulator section, during treatment. Maximum electric field enhancement should be 75 kilovolts per centimeter at any point along the cell, and energy deposition along the centerline at the longitudinal centerline of the cell at a field level at or above 25 kilovolts per centimeter must be at least 80% of the energy deposited along the inner surface of the cell at the longitudinal center of the cell. (Note that the energy deposition along the centerline should be at least 80% of the energy deposition along the inner surface at any point along the cell, but, generally, the greatest disparity in energy deposition along the centerline of the cell versus energy deposition along the inner surface of the cell occurs at the longitudinal center of the cell.). The inner diameter of the electrodes should conform preferably to inner diameters of readily available tubing or piping, and the gap (inner diameter (I.D.$_i$) at the pinch) should be as large as possible consistent with these parameters so as to accommodate high viscosity fluid food products and suspended solids.

Accordingly, the 21.1 millimeter inner diameter (I.D.) of the electrode selected in the embodiments of FIGS. 24 through 28 is about 1 inch, which is the commonly available pipe diameter.

With reference to the electric field plots in FIG. 29, and in particular with respect to the electric field plot for the design of FIG. 24, it is noted that the insulator pinch shields the triple points of the electrodes very well. This is evidenced by the fact that electric field enhancement at the triple points is well below electric field strength in the treatment region of the cell, i.e., essentially in the insulator section. Applying the guidelines set forth above, it is observed in FIG. 29 that the minimum field in the treatment region is about 0.41 volts per centimeter for 1 volt across the electrodes of the cell of FIG. 22. Assuming the minimum effective electric field strength of 25 kilovolts per centimeter, a voltage on the cell of FIG. 22 of 61 kilovolts is thus required, which is well within the guideline set forth above of 100 kilovolts maximum across the cell. At 61 kilovolts across the cell, maximum electric field strength is about 40 kilovolts per centimeter, which is again within the design guideline set forth above of 75 kilovolt per centimeter maximum electric field strength. Energy deposition is expected to be similar to that shown in FIG. 23.

The design of FIG. 25 increases the distance between electrodes by increasing total insulator section length ($l_i$). As corresponding electric field plot of FIG. 29 shows, the shape of the electric field plot curve remains essentially the same for the cell of FIG. 24 and the cell of FIG. 25, but the magnitudes of the electric field strength are reduced for the design of FIG. 24. The electric strength at which the electric field plot curves for electric field strength along the inner surface and along the centerline cross for the cell of FIG. 24 is at 0.37 volts per centimeter for 1 volt across the electrodes, which thus indicates that this cell design requires 68 kilovolts on the cell to yield the 25 kilovolts per centimeter minimum electric field. Thus, it does not appear there is a significant reduction in enhancement in the design of FIG. 25, but higher voltages are required as the electrodes are separated greater distances, i.e., as the total insulator length ($l_i$) increases. In other words, this requirement of higher voltage across the electrodes (which is undesirable) is not offset by significant reductions in triple point enhancement.

With respect to the design of FIG. 26, the electrode separation, i.e., total insulator length ($l_i$), remains the same as in FIG. 25, but the insulator pinch is changed by increasing its length ($l_p$). The transition angle is maintained as the same angle as in FIG. 24.

The effect of increasing the length of the insulator pinch ($l_p$) is dramatic (as opposed to the minor affect achieved in the cell of FIG. 25 by increasing the overall insulator length ($l_i$). Variation between the electric field strength along the centerline and the electric field strength along the inner surface is reduced significantly in the present design. The crossing point of the centerline electric field plot and the inner surface electric field plot is at 0.3 volts per centimeter, which translates into 83 kilovolts on the cell, i.e., across the electrodes. This cell voltage is higher than for the cells of FIGS. 24 and 25, but is still within the guideline of 100 kilovolts set forth above. At 83 kilovolts, the highest fields are only about 40 kilovolts per centimeter, which again is well within the design guidelines of 75 kilovolts per centimeter. Thus, the higher cell voltage is offset in the cell of FIG. 26 by superior electric field distribution (i.e., reduction in electric field enhancement) as compared to the cells of FIGS. 24 and 25.

Figure 30:
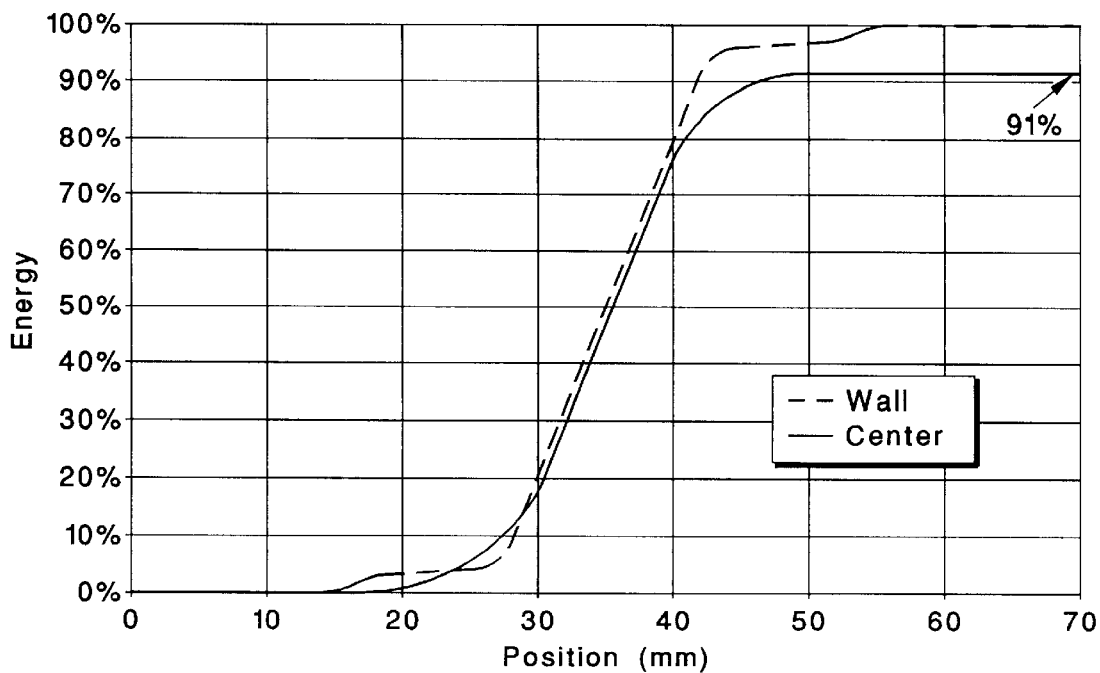
FIG. 30 is a energy deposition plot for the cell design of FIG. 26 showing energy deposition per pulse at an inner surface of the cell and along a centerline of the cell.

Referring next to FIG. 30, one possible drawback to the cell of FIG. 26 is that the slope of the electric field plots, especially the field plot of electric field along the centerline, is less steep than in the designs of FIGS. 24 and 25 which indicates a greater amount of energy deposition at electric field strengths below the minimum electric field strength needed to effect deactivation of microorganisms. An energy deposition calculation relative to FIG. 30 shows that a food product at the centerline is receiving 91% of the energy deposition that food product near the inner surface is receiving when analyzed at the longitudinal center of the cell. Additionally, 86% of the total energy delivered to the food product near the inner surface, and 77% of the total energy delivered to the food product near the centerline is delivered between the electric field plot curve crossing point, i.e., at the electric field level above the threshold of 40 kilovolts per centimeter. The overall ratio of energy deposited along the inner surface to the energy deposited along the centerline in the region of interest is 82%, which is above the guideline 80% established above.

Overall, this cell of FIG. 26 appears to be preferred, assuming fluid flow patterns do not create insurmountable problems, and in particular, assuming downstream flow effects are not too detrimental as the food product passes out of the insulator pinch and transitions to the second electrode.

Referring back to FIG. 29 and to FIGS. 27 and 28, cells are shown that could result in improved flow characteristics.

In FIG. 27, the slope of the insulator in the transition regions is made more gradual, i.e., the slope angle is smaller, than in the cell of FIG. 26.

In FIG. 28, the insulator is made asymmetric, allowing for a more gradual slope in the downstream portion of the insulator, i.e., in the downstream transition region, which could help prevent fluid flow separation.

In the field plots of FIG. 29, the effects of changing the insulator slope in the transition regions is shown in an electric field plot for the cell of FIG. 27. In the design of FIG. 27, the effects on electric field and energy deposition are minor. The field levels are reduced for the cell of FIG. 27, which requires a higher voltage on the chamber, but such voltage is still less than the 100 kilovolt maximum specified above. The slope of the field plot, however, is also less steep, which means that the percentage of total energy deposited above the threshold is less. However, the ratio of energy deposited near the centerline of the cell to the energy deposited near the outer wall of the cell is very good.

Review of FIG. 29 suggests that the design of FIG. 28 is less desirable from an electrical standpoint. For example, the electric field plots are very peaked at the insulator pinch and slope gently at their ends. This indicates a significant portion of the energy being deposited at an electric field strength that is below the threshold electric field for deactivating microorganisms. Choosing a threshold of 0.3 volts per centimeter (which requires 83 kilovolts on the cell to yield 25 kilovolts per centimeter at a threshold point), then 63% of the energy deposited near the inner surface of the cell is above the threshold level. At the centerline, this figure drops to 58%, thus now rendering the embodiment of FIG. 28 relatively inefficient from an electrical standpoint as compared to the embodiments of, for example, FIGS. 26 and 27. Nonetheless, under some circumstances, the embodiment of FIG. 28 may prove advantageous due to its potentially superior flow dynamics.

The following parameters are employed nominally in the descriptions herein:

Treatment chamber resistance is chosen to be 100 ohm centimeters yielding an overall chamber resistance of 274 ohms. Pulse width is selected to be two microseconds, and a charge voltage of 35 kilovolts is used. A square pulse shape is used so as to maximize the amount of energy deposited above a threshold electrical strength. A Rayleigh type of pulse forming network is used for its simplicity of implementation.

EXAMPLE

A cell in accordance with the design illustrated in FIG. 26 is constructed and 0.3 volts per centimeter is selected and a reference point for scaling the electric field, as this is the crossing point for the electric field plot at the centerline of the cell with the electric field plot at the inner surface of the cell. To scale the 0.3 volts per centimeter to 25 kilovolts per centimeter, it is necessary to apply a voltage across the cell, i.e., between the electrodes, of 83.3 kilovolts. At this voltage level, peak fields are examined to insure that they are not so high as to cause breakdowns. FIG. 31 is an electric field plot for the cell of FIG. 26 showing the scaled 0.3 volt per centimeter level and the field enhancement as a function of applied voltage. It can be seen that the maximum enhanced electric field strength at 83.3 kilovolts applied voltage is 39 kilovolts per centimeter, which is considered conservative.

Given that the maximum charge voltage is 35 kilovolts, this implies that a pulse transformer is required. Assuming the impedance of the load is reflected through the pulse transformer to the characteristic impedance of the pulse forming network, for 35 kilovolts of charge, 17 kilovolts will be on the primary of the pulse transformer. The turns ratio is therefore 4.76:1. To simplify and to provide a safety factor, a turns ratio of 5:1 is assumed. As a result, output voltage is 5 times input voltage across the pulse transformer. Conversely, output current is ⅕ the input current.

The inductance and capacitance of the pulse forming network is calculated by solving the following equation:

$$\tau = 2 \cdot \sqrt{LC} \text{ and } Z = \sqrt{\frac{L}{C}}$$

where L is total inductance and C is total capacitance. For a Rayleigh type pulse forming network, the L and C are divided evenly between all stages. The 100 ohm treatment chamber resistance reflected through the transformer gives a pulse forming network impedance of 4 ohms. Solving the above equation yields (L) equal to 8 microhenrys and total capacitance (C) equal to 500 nanofarads.

Selecting a four stage pulse forming network yields the model pulse forming network shown in FIG. 32. Calculated waveforms from this pulse forming network are shown in FIGS. 33 and 34, which show, respectfully, current waveforms (FIG. 33) and voltage waveforms (FIG. 34) for the pulse generator and for the treatment cell. Of note, in FIG. 33, the peak current in the pulse generator is only about 1.75 kiloamps.

Impedance of the treatment chamber determines the current in the switch, which can be a limiting design factor, and determines, to some extent, the pulse shape (square pulses become much easier to produce at higher impedances). The 100 ohm resistance chosen in this example is equivalent to about 36 ohm centimeters of resistivity. In order to make this determination, the treatment chamber of FIG. 26 is divided into three hypothetical sections shown in FIG. 35. If resistance in each section is known, the total resistance is twice the sum of the individual section resistances. As shown in FIG. 35, sections I and III are simple cylinders whose resistances are $$R = \rho\frac{L}{A}$$

where ρ is resistivity, L is the length of the cylinder, and A is the cross-sectional area of the cylinder. A frustoconical section, i.e., Section II, is computed as the sum of resistances of disks of length dx, whose radii vary continuously with position. The sum of the disk resistances is $$R = \frac{\rho}{\pi} \cdot \int_A^B \frac{dx}{(x \cdot \tan(\theta))^2}$$

Using ρ=1, a resistance factor which is equivalent to 1/A can be determined. For the geometry shown, this factor is 2.74. Thus, the resistance of the cell is given by R=2.74×ρ. Rearranging and solving for ρ with R=100 ohms gives ρ=to 36.5 ohm centimeters.

The electric field code gives a result indicating that the resistance for a given resistivity is even higher than shown. This is probably due to the fact that this calculation is a worse case scenario, where the current source is modeled as a plate across the end of the cylinder. In actual design, the electrode is the pipe wall and the resistance is not the same for each point on the pipe wall. Since the pulse generator design is determined by actual resistance of the treatment cell, actual measurements on the cell are required to yield accurate resistance figures.

Energy deposited into the food product stuff during a pulse is proportional to the square of the electric field strength. The electric field is not uniform and, thus, one would not expect energy deposition to be uniform either.

As a method of comparison, the square of the electric field strength is integrated along a path through the chamber. This value represents the energy a volume of product flowing through the path would receive if the field were applied for the entire time the volume is traveling the path. In comparing one path to another, it is assumed that the volume units are traveling through the chamber at the same velocity. (This is not generally the case, therefore, curves such as those in FIG. 30 should be used as a general quality comparison and not as a precise indication of energy deposition.)

Figure 31:
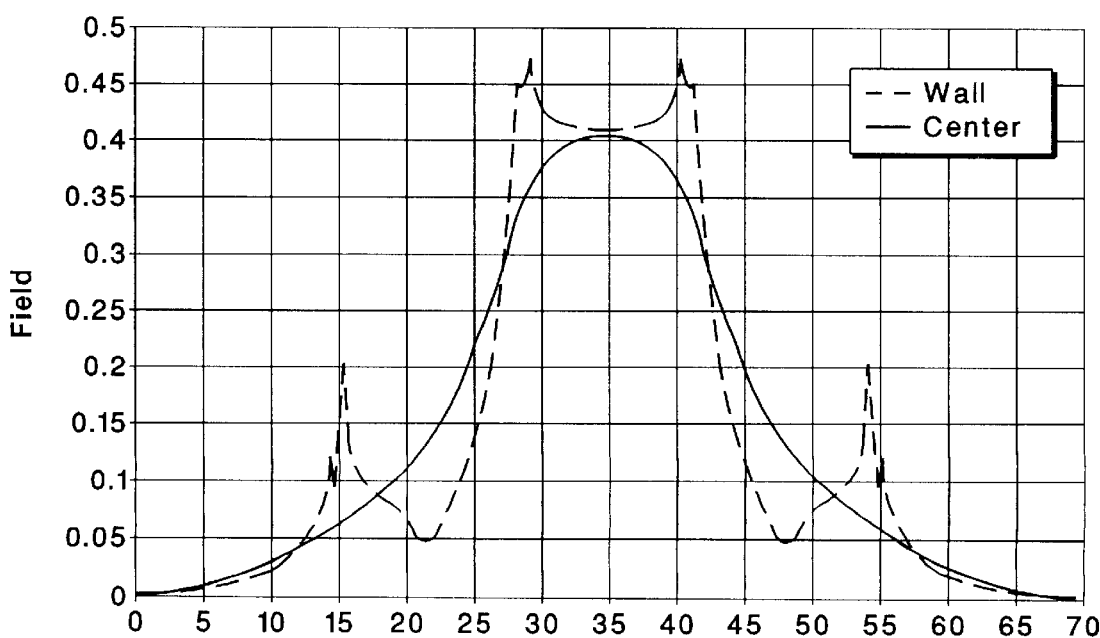
FIG. 31 is an electric field plot for the cell design of FIG. 26 showing electric field strength at an inner surface of and along a centerline of the cell designs of FIGS. 24 through 28.
Figure 32:
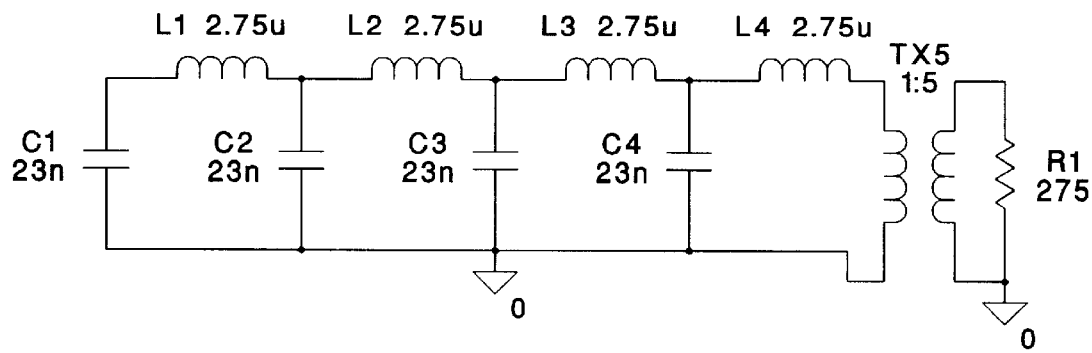
FIG. 32 is a schematic diagram showing a circuit model of a pulse forming network suitable for use in embodiments of the pulsed field treatment apparatus of FIG. 1.
Figure 35:
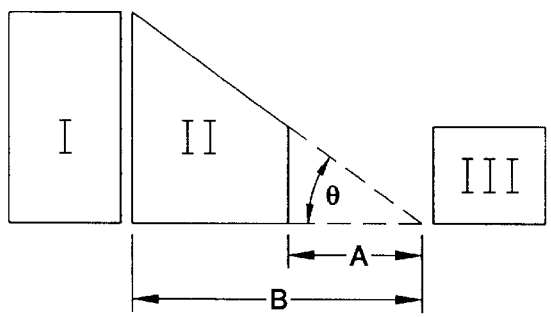
FIG. 35 is a schematic diagram showing treatment chamber (or cell) sections of the cell design of FIG. 26 used in resistance calculations.
Figure 33:
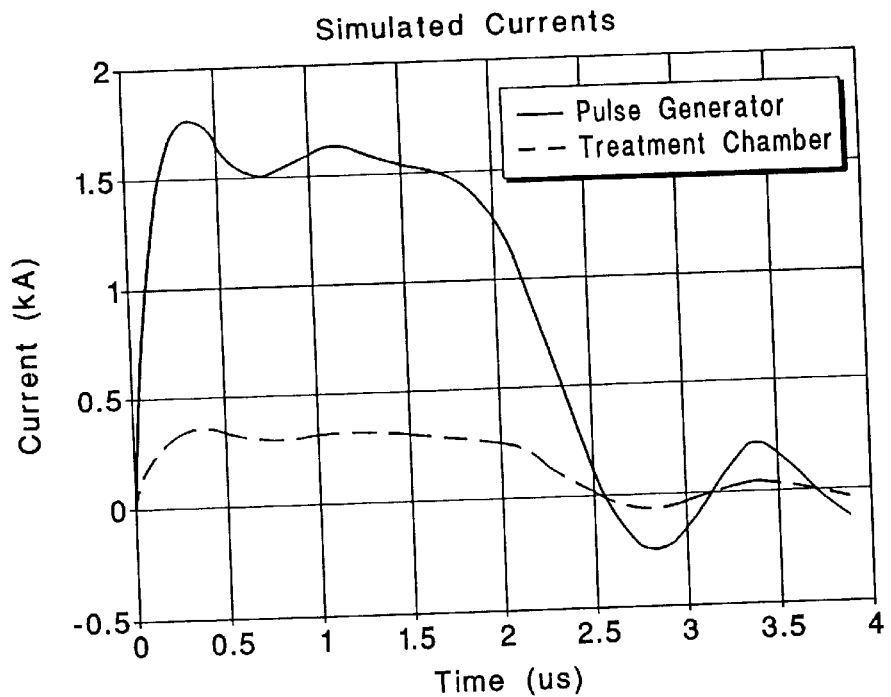
FIG. 33 is a current waveform for an electric pulse supplied to the cell design of FIG. 26 showing current through a pulse generator and current through the cell.
Figure 34:
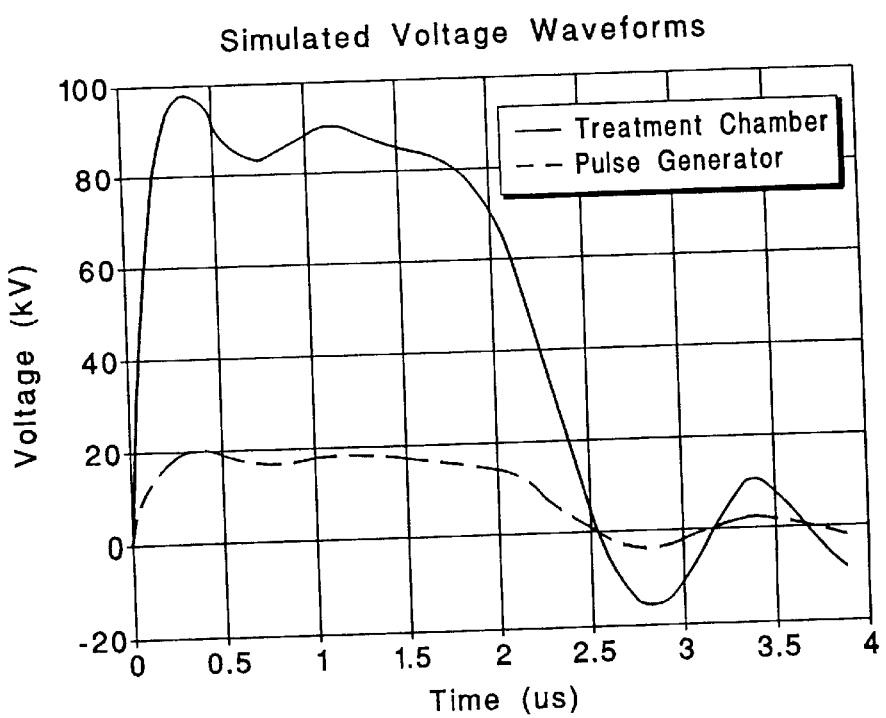
FIG. 34 is a voltage waveform for the electric pulse applied to the cell design of FIG. 26 showing voltage across the pulse generator and voltage across the cell.

Note that, as shown in FIG. 30, for the geometry of FIG. 26, a volume traveling down the centerline of the cell will receive 91% of the energy received by a volume traveling along the inner surface of the cell. (This is without velocity correction.) From this, a calculation can also be made as to the percentage of energy that is deposited above the chosen minimum electric field strength for deactivation. In the present case, 77% of the energy deposited along the centerline of the cell is deposited between about 27 millimeters and 42 millimeters. Referring to the field plot in FIG. 31, it is noted that this is where the electric field strength plots cross the 0.3 volt per centimeter mark, which is the chosen value or threshold field. Along the outer wall, the figure is 86%.

As mentioned above, these numbers do not account for velocity differences in the food product flow. For specific cell designs, such as has been disclosed above, one can calculate a number of electrical pulses each volume will receive and the approximate position of a particular volume amount when each pulse arrives. This provides a more accurate picture of the uniformity of treatment, i.e., uniformity of energy deposition. To make these calculations, it is assumed that fluid product flow is laminar. Furthermore, an average treatment level and electric pulse rate necessary to provide such average treatment level are determined. As the number of pulses received by the volume element increases, average treatment level increases as well. At its limit, the energy profiles shown in FIG. 30 are obtained.

For purposes of this example, a treatment level of 41.8 joules per millimeter is selected. This corresponds to a temperature rise in the product of about 10° C., assuming the product characteristics are similar to those of water.

The energy per electrical pulse can be calculated from the capacitance of the pulse forming network and the charge voltage assuming 100% energy transfer efficiency using:

$$\text{Energy} = \frac{1}{2} \times CV^2,$$

where C is the total capacitance of the pulse forming network (92 nanofarads in the present example) and V is the charge voltage (35 kilovolts in the present example). Energy per pulse is thus 56 joules.

Next a flow rate is selected. In the transition region, flow may somewhat randomly move between laminar and turbulence, however, laminar flow is assumed throughout herein. The following analysis, thus, assumes a straight pipe for purposes of ease of calculation. (The fact that the narrow pinched insulator portion of the cell is close to the transition region may cause flow characteristics which cannot be readily characterized as laminar or turbulent, i.e., the flow may be in a transition state even at a calculated Reynolds number of less than 2000 liters per hour.) For purposes of this example, a flow rate of 1000 liters per hour is selected, which is well below the transition region, (i.e., which is well below 2000 liters per hour). With a flow rate of 1000 liters per hour and an energy deposition of 41.8 joules per milliliter, one can calculate the power required to be 11.6 kilowatts. With 56 joules per pulse, this means 207 pulses per second are needed. At a flow rate of 1000 liters per hour, average velocity in the pinched insulator region is 354 millimeters per second and the peak velocity is nearly 708 centimeters per second.

Laminar flow in a cylindrical pipe has a parabolic velocity distribution with a peak velocity on the centerline equal to twice average velocity. Velocity at the outer wall is zero. As the flow approaches turbulence, the parabola flattens out approaching plug flow. The peak velocity at that point, is less than twice the average velocity.

For the present example, it is assumed that parabolic flow is present and energy per unit volume is calculated for flow on the centerline. The energy for a volume at the average velocity is the nominal value chosen of 41.8 joules per milliliter.

It is assumed that an electrical pulse is applied when volume of interest is at a zero milliliter point along the length of the cell. At a velocity of 354 centimeters per second and a time between pulses of 4.8 milliseconds, position of this volume as each succeeding pulse is applied, can be calculated. Then, energy being applied can be calculated as $$\text{Energy} = \frac{E^2 \times \tau}{\rho}.$$

These values are summarized in Table 1 below:

TABLE 1

| Pulse Number | Position (mm) | Energy (J/ml/pulse) |
|---|---|---|
| 1 | 0 | .00057 |
| 2 | 17.1 | .812 |
| 3 | 34.2 | 34.2 |
| 4 | 51.3 | 1.12 |
| 5 | 68.4 | .0009 |

Total energy deposition for a volume on the centerline entering the treatment cell just as the first pulse is applied is 36.13 Joules per milliliter or 86% of the average energy deposition. Examining an alternative volume already in the cell when the first pulse is applied results in the energy deposition as summarized in Table 2 below:

TABLE 2

| Pulse Number | Position (mm) | Energy (J/ml/pulse) |
|---|---|---|
| 1 | 8.55 | .065 |
| 2 | 26.65 | 8.33 |
| 3 | 42.75 | 14.09 |
| 4 | 59.85 | .11 |

This is a worst case with only 22.6 Joules per milliliter or 54% of average energy.

The values given in the tables are approximations as the actual velocity is not constant over the entire length of the treatment chamber. Actual energy deposition values are probably higher.

While the invention herein disclosed has been described by means of specific embodiments and applications thereof, numerous modifications and variations could be made thereto by those skilled in the art without departing from the scope of the invention as set forth in the claims.

What is claimed:

1. A pulsed electric field treatment system for deactivating organisms in a fluid product, the system comprising:
   a first electrode for applying a voltage to produce a pulsed electric field;
   an insulator section coupled to the first electrode, the insulator section including an insulator pinch, an opening, and a transition region interposed thereinbetween, the opening having a larger cross-sectional area than the insulator pinch, the insulator section including a cavity, passing through the insulator pinch, the transition region, and the opening, wherein the fluid product is contained during deactivating of organisms; and
   a second electrode for applying the voltage to produce the pulsed electric field, coupled to the insulator section, wherein the first electrode is positioned on a first side of the insulator pinch, and the second electrode is positioned on a second side of the insulator pinch, wherein the pulsed electric field is formed between the first electrode and the second electrode, when the voltage is applied across the first electrode and the second electrode, and passes through the insulator pinch.

2. The system of claim 1 further comprising:
   a pulse forming network coupled to the first electrode and the second electrode, wherein a voltage from the pulse forming network is selectively applied across the first electrode and the second electrode.

3. The system of claim 2 further comprising:
   a switch coupled between the pulse forming network and the first electrode, wherein the switch selectively applies the voltage from the pulse forming network across the first electrode and the second electrode.

4. The system of claim 3 further comprising:
   a controller coupled to said switch, wherein the controller selectively controls said switch to apply the voltage from the pulse forming network.

5. The system of claim 4 wherein said pulse forming network includes means for applying a very high electric field strength pulse to said product, said electric field strength pulse having an electric field strength of at least 100 volts per centimeter.

6. The system of claim 5 wherein said controller includes means for controlling said switch to apply said electric field strength pulse for a short duration, the short duration being no more than 100 microseconds.

7. The system of claim 1 wherein said insulator section further includes:
   another opening; and
   another transition region interposed between the other opening and the insulator pinch, the other opening having a larger cross-sectional area than the insulator pinch, the cavity passing through the other transition region, and the other opening.

8. The system of claim 7 wherein said transition region and said other transition region are frustoconical.

9. The system of claim 1 further comprising:
   a flash shield encircling an exterior of the insulator section, the flash shield being between the first electrode and the second electrode, whereby the flash shield inhibits arcing between said first electrode and said second electrode.

10. The system of claim 9 wherein said flash shield has an outer diameter at least twice an outer diameter of said first electrode.

11. The system of claim 1 wherein said transition region between said first electrode and said insulator pinch includes an angle of at least 100 degrees measured from an interior wall of the first electrode to an interior surface of the transition region.

12. The system of claim 1 wherein said first electrode, said transition region, said insulator pinch, and said second electrode are circular in interior cross-sectional.

13. The system of claim 1 wherein said transition region between said first electrode and said insulator pinch include an angle of at least 170 degrees measured from an interior wall of the first electrode to an interior surface of the transition region at an interface between the first electrode and the transition region, and further include an angle of at least 100 degrees measured from an interior wall of the first electrode to an interior surface of the transition region at a point other than at the interface between the first electrode and said transition region.

14. A method of deactivating microorganisms comprising:
   flowing a product containing the microorganisms past a first electrode having a first cross-sectional area;
   flowing the product containing the microorganisms through an insulator section having a second cross sectional area, wherein the second cross-sectional area is smaller than the first cross-sectional area;
   flowing the product containing the microorganisms past a second electrode; and
   applying an electric pulse across the first electrode and the second electrode, including directing an electric field through the insulator section including increasing the electric field density over at least a portion of the insulator section, wherein said electric field has an electric field strength of at least 100 volts per centimeter;
   whereby at least a portion of the microorganisms are deactivated as a result of the applying of the high voltage as the product passes through insulator section.

15. A pulsed electric field treatment system for deactivating microorganisms in a pumpable fluid product comprising:
   a first substantially cylindrical electrode section for applying a voltage to produce a pulsed electric field, the first substantially cylindrical electrode having a first inner diameter;

an insulator section juxtaposed with the first substantially cylindrical electrode section to form a conduit, the insulator section having a second diameter, the second inner diameter being at least ten percent less than the first inner diameter;
a second substantially cylindrical electrode section for applying the voltage to produce the pulsed electric field, the second substantially cylindrical electrode being juxtaposed with the insulator section and further forming the conduit, the second substantially cylindrical electrode section having a third inner diameter, the second inner diameter being at least ten percent less than the third inner diameter; and
a pulser, coupled to the first substantially cylindrical electrode section, and the second substantially cylindrical electrode section, wherein the pulser provides an electric field between said first substantially cylindrical electrode and said second substantially cylindrical electrode having an electric field strength of at least 100 volts per centimeter.

16. The system of claim 15 wherein said pulser includes a pulse forming network, a switch and a controller.

17. The system of claim 16 wherein said pulse forming network includes means for applying a very high electric field strength pulse to said product, said very high electric field strength pulse having an electric field strength of at least 100 volts per centimeter.

18. The system of claim 17 wherein said controller includes means for controlling said switch to apply said very high electric field strength pulse for a short duration, the short duration being no more than 100 microseconds.

19. The system of claim 15 further comprising:
a flash shield encircling an exterior of the insulator section, the flash shield being between the first electrode and the second electrode, whereby the flash shield inhibits arcing between said first electrode and said second electrode.

20. The system of claim 15 wherein said insulator section includes a transition region and an insulator pinch, said transition region being between said first electrode and said insulator pinch and including an angle of at least 100 degrees measured from an interior wall of the first electrode to an interior surface of the transition region.

21. The pulsed electric field treatment system of claim 1 further comprising:
a pulse generator coupled to the first electrode and the second electrode, wherein an applied voltage from the pulsed generator is selectively applied across the first electrode and the second electrode.

22. The pulsed electric field treatment system of claim 1 wherein the first electrode, the second electrode and the insulator section are, further shaped such that fluid product flowing thereinbetween has a laminer flow.

23. The pulsed electric field treatment system of claim 22 wherein the transition region of the insulator section comprises a curved inner wall.

24. The pulsed electric field treatment system of claim 23 wherein the first electrode comprises a first linear inner wall and the second electrode comprises a second linear inner wall.

25. The pulsed electric field treatment system of claim 24 wherein the first linear inner wall and the second linear inner wall intersect the curved inner wall at an angle of at least 170 degrees measured from a tangent on the curved inner wall.

26. The pulsed electric field treatment system of claim 1 further comprising:
a channel formed within the first electrode, the second electrode and the insulator section wherein the fluid product has a laminer flow within the channel.

27. A system for deactivating organisms in a fluid product, the system comprising:
a first electrode;
an insulator section coupled to the first electrode, the insulator section including an insulator pinch, an opening, and a transition region interposed thereinbetween, the opening having a larger cross sectional area than the insulator pinch, the insulator section including a cavity, passing through the insulator pinch, the transition region, and the opening, wherein the fluid product is contained during deactivating of organisms;
a second electrode coupled to the insulator section, wherein the first electrode is positioned on a first side of the insulator pinch, and the second electrode is positioned on a second side of the insulator pinch, whereby an electric field formed between the first electrode and the second electrode, when a voltage is applied across the first electrode and the second electrode, passes through the insulator pinch; and
a flash shield encircling an exterior of the insulator section; the flash shield being between the first electrode and the second electrode whereby the flash shield inhibits arcing between the first electrode and the second electrode.

28. The system of claim 27 further comprising:
a pulse forming network coupled to the first electrode and the second electrode, wherein a voltage from the pulse forming network is selectively applied across the first electrode and the second electrode.

29. The system of claim 27 wherein the transition region is frustoconical.

30. A system for deactivating organisms in a fluid product, the system comprising:
a first electrode;
an insulator section coupled to the first electrode, the insulator section including an insulator pinch, an opening, and a transition region interposed thereinbetween, the opening having a larger cross sectional area than the insulator pinch, the insulator section including a cavity, passing through the insulator pinch, the transition region, and the opening, wherein the fluid product is contained during deactivating of organisms;
a second electrode coupled to the insulator section, wherein the first electrode is positioned on a first side of the insulator pinch, and the second electrode is positioned on a second side of the insulator pinch, whereby an electric field formed between the first electrode and the second electrode, when a voltage is applied across the first electrode and the second electrode, passes through the insulator pinch; and
wherein the transition region between the first electrode and the insulator pinch includes an angle of at least 170 degrees measured from an interior wall of the first electrode to an interior surface of the transition region at an interface between the first electrode and the transition region, and further includes an angle of at least 100 degrees measured from an interior wall of the first electrode to an interior surface of the transition region at a point other than at the interface between the first electrode and said transition region.

31. The system of claim 30 further comprising:
a pulse forming network coupled to the first electrode and the second electrode, wherein a voltage from the pulse forming network is selectively applied across the first electrode and the second electrode.

32. The system of claim 31 wherein the transition region is frustoconical.

33. A system for deactivating microorganisms in a pumpable fluid product comprising:

a first substantially cylindrical electrode section having a first inner diameter;

an insulator section juxtaposed with the first substantially cylindrical electrode section to form a conduit, the insulator section having a second diameter, the second inner diameter being at least ten percent less than the first inner diameter;

a second substantially cylindrical electrode section juxtaposed with the insulator section and further forming the conduit, the second substantially cylindrical electrode section having a third inner diameter, the second inner diameter being at least ten percent less than the third inner diameter; and a pulser coupled to the first substantially cylindrical electrode section;

wherein the insulator section includes a transition region and an insulator pinch, the transition region being between the first electrode and the insulator pinch and including an angle of at least 100 degrees measured from an interior wall of the first electrode to an interior surface of the transition region.

34. The system of claim 33 wherein said pulser includes a pulse forming network, a further comprising:

a switch coupled between the pulser and the first electrode, wherein the switch selectively applies the voltage from the pulser across the first electrode and the second electrode.

35. The system of claim 33 further comprising:

a controller coupled to the switch, wherein the controller selectively controls the switch to apply the voltage from the pulser.

36. The system of claim 33 wherein said pulser includes means for applying a pulse to the fluid product, the pulse having an electric field strength of at least 100 volts per centimeter.

37. The system of claim 36 wherein the controller includes means for controlling the switch to apply the pulse for a short duration, the short duration being no more than 100 microseconds.

38. The system of claim 33 wherein the insulator section further includes:

an insulator pinch, an opening, and a transition region interposed thereinbetween, the opening having a larger cross sectional area than the insulator pinch, the insulator section including the conduit, the conduit passing through the insulator pinch, the transition region, and the opening, wherein the fluid product is contained during deactivation of organisms; and a further wherein the first substantially cylindrical electrode is positioned on a first side of the insulator pinch, and the second substantially cylindrical electrode is positioned on a second side of the insulator pinch, wherein a pulsed electric field is formed between the first substantially cylindrical electrode and the second substantially cylindrical electrode, and passes through the insulator pinch.

39. The system of claim 33 wherein the insulator section further includes:

another opening; and another transition region interposed between the other opening and the insulator pinch, the other opening having a larger cross sectional area than the insulator pinch, the cavity passing through the other transition region, and the other opening.

40. The system of claim 33 wherein the transition region and the other transition region are frustoconical.

41. The system of claim 33 wherein the first substantially cylindrical electrode, the transition region, the insulator pinch, and the second substantially cylindrical electrode are circular in interior cross section.

42. The system of claim 33 wherein the transition region between the first substantially cylindrical electrode and the insulator pinch further includes an angle of at least 170 degrees measured form the interior wall to the interior surface.

43. The system of claim 1 wherein the transition region is frustoconical.

* * * * *

UNITED STATES PATENT AND TRADEMARK OFFICE
CERTIFICATE OF CORRECTION

PATENT NO : 6,110,423
DATED : 8/29/2000
INVENTOR(S) : Bushnell, et al.

It is certified that an error appears in the above-identified patent and that said Letters Patent are hereby corrected as shown below:

IN THE CLAIMS:

At column 22, lines 47-48, replace "cross sectional" with --cross-sectional-- (see page 3, claim 14, of Amendment under §1.312).

At column 23, line 50, replace "are, further" with - are further- (see line 1 of page 5, claim 22 of Amendment under §1.111).

At column 25, line 30, replace "network, a further comprising" with --network, the system further comprising--.

At column 26, line 13, replace "a further wherein" with --further wherein--.

At column 26, line 39, replace "form" with --from--.

Signed and Sealed this

Fifteenth Day of May, 2001

*Attest:*

NICHOLAS P. GODICI

*Attesting Officer*  *Acting Director of the United States Patent and Trademark Office*

UNITED STATES PATENT AND TRADEMARK OFFICE
CERTIFICATE OF CORRECTION

PATENT NO. : 6,110,423
DATED : August 29, 2000
INVENTOR(S) : Bushnell et al.

It is certified that error appears in the above-identified patent and that said Letters Patent is hereby corrected as shown below:

Column 22,
Lines 47-48, replace "cross sectional" with -- cross-sectional --.

Column 23,
Line 50, replace "are, further" with -- are further --.

Column 25,
Line 30, replace "network, a further comprising" with -- network, the system further comprising --.

Column 26,
Line 13, replace "a further wherein" with -- further wherein --.
Line 39, replace "form" with -- from --.

Signed and Sealed this

Twenty-first Day of September, 2004

JON W. DUDAS
*Director of the United States Patent and Trademark Office*